(12) United States Patent
Campbell et al.

(10) Patent No.: US 11,929,164 B2
(45) Date of Patent: *Mar. 12, 2024

(54) COMPUTER IMPLEMENTED SYSTEM AND METHOD FOR VISUALLY DISPLAYING INSTANCES OF INCREASED SUSCEPTIBILITY FOR COMMISSION OF MEDICAL ERRORS

(71) Applicant: The University of South Alabama, Mobile, AL (US)

(72) Inventors: Amy Ashe Campbell, Spanish Fort, AL (US); Christopher Todd Harlan, Daphne, AL (US); Stephen Matthew Campbell, Spanish Fort, AL (US)

(73) Assignee: The University of South Alabama

( * ) Notice: Subject to any disclaimer, the term of this patent is extended or adjusted under 35 U.S.C. 154(b) by 215 days.

This patent is subject to a terminal disclaimer.

(21) Appl. No.: 17/360,393

(22) Filed: Jun. 28, 2021

(65) Prior Publication Data

US 2021/0327568 A1 Oct. 21, 2021

Related U.S. Application Data

(63) Continuation of application No. 16/295,994, filed on Mar. 7, 2019, now Pat. No. 11,087,874.

(Continued)

(51) Int. Cl.
*G16H 40/20* (2018.01)
*G06Q 10/0631* (2023.01)
(Continued)

(52) U.S. Cl.
CPC ..... *G16H 40/20* (2018.01); *G06Q 10/063114* (2013.01); *G06Q 10/0635* (2013.01); *G06Q 10/06398* (2013.01); *G16H 15/00* (2018.01)

(58) Field of Classification Search
CPC ........ G06Q 10/0635; G06Q 10/06398; G06Q 10/063114; G16H 40/20; G16H 15/00; G16H 10/60
See application file for complete search history.

(56) References Cited

U.S. PATENT DOCUMENTS 8,515,777 B1 * 8/2013 Rajasenan .............. G16H 50/30
705/7.14
2004/0064341 A1 * 4/2004 Langan .................. G16H 15/00
705/2

(Continued)

*Primary Examiner* — Mark Holcomb
(74) *Attorney, Agent, or Firm* — AdamsIP, LLC; J. Hunter Adams; Edward B. Garner, III

(57) ABSTRACT

Systems and methods for visually displaying instances of increased susceptibility for commission of medical errors are provided. Execution of programming instructions on a computer-readable medium causes a processor to retrieve historical workload data corresponding to environmental conditions experienced by and near misses associated with an individual or team of individuals during a first period of time from one or more data repositories. Retrieved workload data is processed to establish threshold limits for distinct working conditions represented within the workload data for the individual or team of individuals. Workload data corresponding to a second period of time is retrieved for the individual or team of individuals and compared to established threshold limits by the processor. Based on the comparison, the processor generates one or more displayable indicia indicative of the individual's or team of individuals' risk of committing a medical error due to an experienced workload.

20 Claims, 11 Drawing Sheets

Related U.S. Application Data

(60) Provisional application No. 62/639,902, filed on Mar. 7, 2018.

(51) Int. Cl.
*G06Q 10/0635* (2023.01)
*G06Q 10/0639* (2023.01)
*G16H 15/00* (2018.01)

(56) References Cited

U.S. PATENT DOCUMENTS

| | | | | |
|---|---|---|---|---|
| 2005/0055242 A1* | 3/2005 | Bello | ............... | G16H 20/17 |
| | | | | 705/2 |
| 2018/0122506 A1* | 5/2018 | Grantcharov | .......... | G16H 50/50 |

* cited by examiner

| 511 | | 910 | 915 |
|---|---|---|---|
| | Healthcare Professional: Amy Applicant | | 1/21/2018 3:02 PM |
| 920A | Task Count | R ○ 〇 Y ⦿ 925 G ● | Medium Risk:4-5  930A High Risk:>5  930B | Actual: 3  935 |
| 920B | Patient Count | ⦿ ○ ● | Medium Risk:7-8 High Risk:>8 | Actual: 8 |
| 920C | Acuity Score | ⦿ ○ ● | Medium Risk:5-7 High Risk:>7 | Actual: 4 |
| 920D | Work Schedule | ⦿ ○ ● | Medium Risk:7-9 High Risk:>9 | Actual: 6 |
| 920E | Med Count | ⦿ ○ ● | Medium Risk:10-12 High Risk:>12 | Actual: 9 |
| 920F | Call Light Count | ⦿ ○ ● | Medium Risk:3-4 High Risk:>4 | Actual: 5 |
| 920G | Hours Worked | ⦿ ○ ● | Medium Risk:40-45 High Risk:>45 | Actual: 39 |

COMPUTER IMPLEMENTED SYSTEM AND METHOD FOR VISUALLY DISPLAYING INSTANCES OF INCREASED SUSCEPTIBILITY FOR COMMISSION OF MEDICAL ERRORS

CROSS REFERENCES TO RELATED APPLICATIONS

This application is a continuation of a co-pending U.S. patent application Ser. No. 16/295,994 filed Mar. 7, 2019, which claims priority to U.S. Provisional Application Ser. No. 62/639,902 filed on Mar. 7, 2018, in which both applications are incorporated herein in their entirety by reference.

FIELD OF THE DISCLOSURE

The subject matter of the present disclosure refers generally to a computer implemented system and method for visually displaying instances of increased susceptibility for commission of medical errors.

BACKGROUND

While the introduction of new technologies into the healthcare environment has allowed healthcare professionals to become more efficient at their jobs, the responsibilities and general workload of healthcare professionals has increased significantly in recent years. Currently, fewer professionals are being expected to handle this increased workload because hospitals often manage their costs by decreasing the size of their staff. In turn, those staff members retaining employment are generally required to care for an increased number of patients and work longer hours. Moreover, reduced staffing compounded with additional work expectations may also lead to a decrease in the number of direct nurse-patient care hours each patient receives from their healthcare provider. As a result, hospital floors experiencing higher workloads at various times of the day will generally have higher incidences of patient mortality, increased commission of medical and medication errors, more frequent patient complications, and/or lower patient satisfaction during high workload periods as each are directly related to the number of direct nurse-patient care hours received.

Moreover, when a nurse's workload increases due to patient count, call lights, or otherwise, nurses are personally affected due to higher levels of work-related stress. Increased work-related stress generally causes nurses to experience increased levels of anxiety, fatigue, and burnout, which can lead to decreased job satisfaction and nurse retention. This, in turn, negatively affects the quality of care that patients receive even when they do receive direct nurse-patient care.

Because direct nurse-patient care hours are generally determined based on monthly averages for the specialty or type of care given on each unit, identifying specific factors adversely affecting a healthcare professional's work in real time has been extraordinarily difficult if not impossible. Though healthcare management generally attempts to distribute work among healthcare professionals as evenly as possible, they are generally unable to account for every action that every healthcare professional within the facility is undertaking at any given time. For instance, during periods of high patient volume, charge nurses are often busy assigning new patients, assisting high workload nurses, dealing with patient and family concerns, and addressing doctors' needs. As a result, charge nurses are often unaware of changes to the doctors' orders that may increase the workload of a nurse. In turn, charge nurses unaware of the increased workload resulting from a change in the doctor's orders may inadvertently increase a nurse's already heavy workload. As made clear by the foregoing example, the workloads experienced by healthcare professionals often extend beyond the effective workload that they can comfortably and effectively endure despite the best efforts of management.

In addition, each healthcare professional has different strengths and weaknesses, which impact the way they respond to certain situations. For instance, some healthcare professionals may handle large patient counts or high acuity patients effectively while other professionals may suffer a performance decrease. Some healthcare professionals may be able to process call light interruptions or frequent order changes without losing focus, while other healthcare professionals may be greatly impacted. Because these strengths and weakness vary from professional to professional, it can be difficult for management to create a team of healthcare professionals that complement one another's strengths and minimizes each other's weaknesses. Consequently, this may lead management to unintentionally create teams of healthcare professionals that exacerbates the weaknesses of a healthcare professional, increasing the risk of medical related errors.

SUMMARY

Systems and methods for visually displaying instances of increased susceptibility for commission of medical errors are provided. In an embodiment, the system comprises at least one non-transitory computer-readable medium containing programming instructions executable by at least one computer processor to perform a method which, upon execution, generates displayable indicia indicative of the degree in which an individual or team of healthcare professionals are susceptible to committing a medical error due to their experienced workload.

In an embodiment, the method includes one or more processors retrieving workload data corresponding to environmental working conditions experienced by one or more individuals and the near-miss data corresponding to instances of an averted medical error associated with those individuals during a first specified period of time from one or more repositories, such as an Electronic Health Record (EHR) database and/or Barcode Medication Administration (BCMA) database. Based on the retrieved data, one or more processors may, in some embodiments, calculate at least one threshold limit for each distinct working condition within the retrieved workload data for the one or more individuals. Each threshold limit represents a quantitative threshold corresponding to the amount of a specific working condition that a specific individual can tolerate within their workload before experiencing an increased risk for committing a medical error. A second set of workload data corresponding to the environmental working conditions experienced by the one or more individuals during a second period of time is retrieved by one or more processors to account for the working conditions defining the one or more individuals' workload at a specific point in time. The working conditions experienced by each of the one or more individuals during the second period of time are compared to threshold limits corresponding to such working conditions by one or more processors using the second set of workload data to determine whether one or more aspects of their experienced workload is subjecting the one or more individuals to an increased risk of committing a medical error. Based on the comparison of the second set of workload data to the threshold limits of the one or more individuals, one or more processors may then generate one or more displayable indicia indicative of whether the one or more individuals are at an increased risk of committing a medical error based on their experienced workload. The one or more displayable indicia may be subsequently displayed to users via the user interface of one or more computing devices operably connected to the one or more processors.

In some embodiments, one or more steps of the methods of the present disclosure may be reiterated to account for changes in the working conditions of the one or more individuals' workload, to update the threshold limits associated with each individual, and/or to update or generate new displayable indicia. In an embodiment, certain steps of the methods of the present disclosure may be reiterated in accordance with a defined time schedule. In one embodiment, the steps of the method including retrieving a second set of workload data, comparing the second set of workload data to corresponding threshold limits, and generating displayable indicia may be reiterated at defined intervals such that displayable indicia is generated in substantially real time. In some embodiments, the system of the present disclosure may further comprise a user interface, one or more computing devices operably connected to the processor, one or more data repositories, and/or one or more devices operably connected to one or more data repositories.

These and additional features provided by the embodiments of the present disclosure will be more fully understood in view of the following detailed description, in conjunction with the drawings.

DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 9B shows a screen display presented on a user interface in accordance with one embodiment consistent with the principles of the present disclosure.

DETAILED DESCRIPTION

In the Summary above and in this Detailed Description, and the claims below, and in the accompanying drawings, reference is made to particular features, including method steps, of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with/or in the context of other particular aspects of the embodiments of the invention, and in the invention generally.

The term "comprises" and grammatical equivalents thereof are used herein to mean that other components, steps, etc. are optionally present. For example, a system "comprising" components A, B, and C can contain only components A, B, and C, or can contain not only components A, B, and C, but also one or more other components. As used herein, the term "medical error" and grammatical equivalents thereof refer to instances where the resulting outcome or execution of a course of action deviates from the intended outcome or planned course of action relating to a medical matter due to an error on the part of the responsible healthcare professional. A medical error may include, but is not limited to, errors related to medication administration or dosage, failure to follow hospital policy, failure to provide or improper documentation of a medically related matter, negative patient response to anesthesia, hospital-acquired infections, missed or delayed diagnosis, avoidable delays in treatment, inadequate follow-up after treatment, inadequate monitoring of patients after procedures, failure to take appropriate action in response to test results, failure to follow proper precautions, and technical errors. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Figure 1:
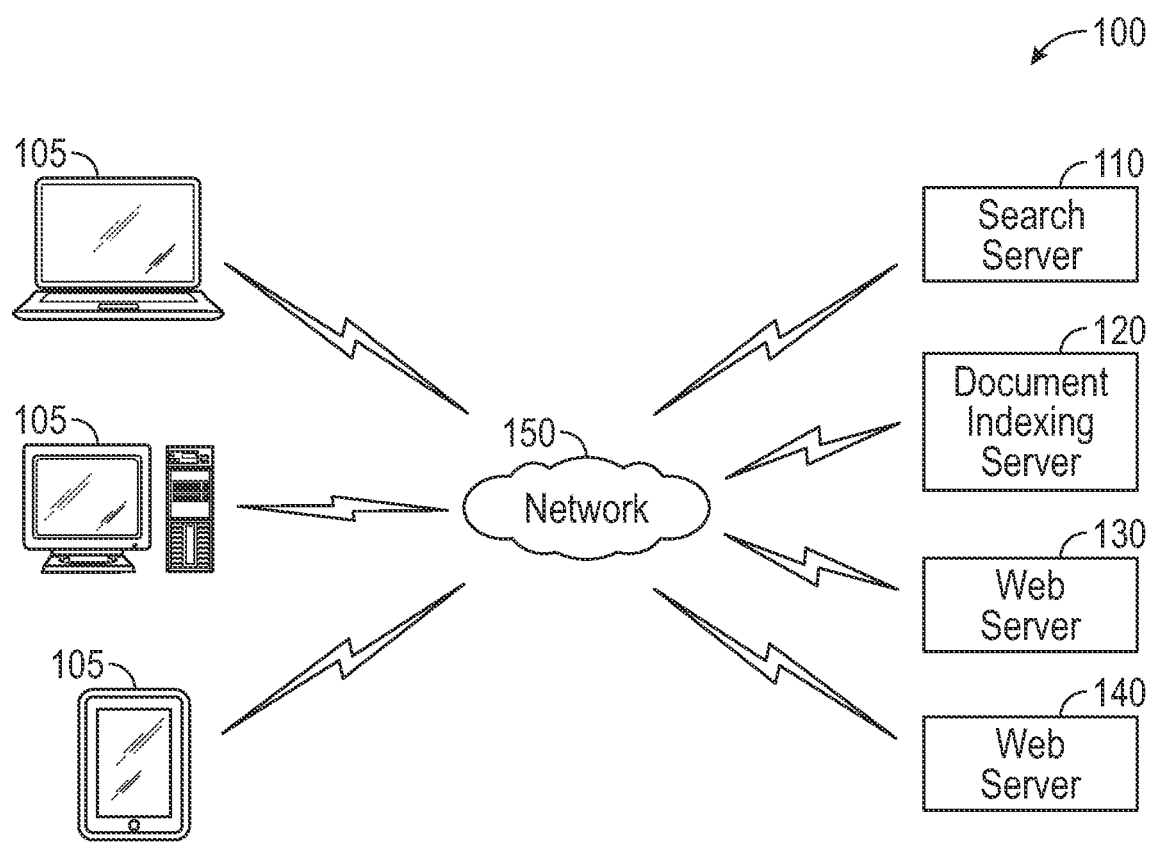
FIG. 1 is a diagram of an example environment in which techniques described herein may be implemented.

FIG. 1 is a diagram of an example environment 100 in which techniques described herein may be implemented. Environment 100 may include multiple clients 105 connected to one or more servers 110-140 via a network 150. In some implementations, and as illustrated, server 110 may be a search server, that may implement a search engine; and server 120 may be a document indexing server, e.g., a web crawler; and servers 130 and 140 may be general web servers, such as servers that provide content to clients 105. Clients 105 and servers 110-140 may be connected to network 150 via wired, wireless, or a combination of wired and wireless connections.

Three clients 105 and four servers 110-140 are illustrated as connected to network 150 for simplicity. In practice, there may be additional or fewer clients and servers. Also, in some instances, a client may perform the functions of a server and a server may perform the functions of a client.

Clients 105 may include devices of users that access servers 110-140. A client 105 may include, for instance, a personal computer, a wireless telephone, a personal digital assistant (PDA), a laptop, a smart phone, a tablet computer, or another type of computation or communication device. Servers 110-140 may include devices that access, fetch, aggregate, process, search, provide, and/or maintain documents. Although shown as single components 110, 120, 130, and 140 in FIG. 1, each server 110-140 may, in some implementations, be implemented as multiple computing devices, which potentially may be geographically distributed.

Search server 110 may include one or more computing devices designed to implement a search engine, such as a documents/records search engine, general webpage search engine, etc. Search server 110 may, for example, include one or more web servers to receive search queries and/or inputs from clients 105, search one or more databases in response to the search queries and/or inputs, and provide documents or information, relevant to the search queries and/or inputs, to clients 105. In some implementations, search server 110 may include a web search server that may provide webpages to clients 105, where a provided webpage may include a reference to a web server, such as one of web servers 130 or 140, at which the desired information and/or links is located. The references, to the web server at which the desired information is located, may be included in a frame and/or text box, or as a link to the desired information/document.

Document indexing server 120 may include one or more computing devices designed to index documents available through network 150. Document indexing server 120 may access other servers, such as web servers that host content, to index the content. In some implementations, document indexing server 120 may index documents/records stored by other servers, such as web servers 130 and 140 and, connected to network 150. Document indexing server 120 may, for example, store and index content, information, and documents relating to user accounts and user-generated content.

Web servers 130 and 140 may each include web servers that provide webpages to clients. The webpages may be, for example, HTML-based webpages. A web server 130/140 may host one or more websites. A website, as the term is used herein, may refer to a collection of related webpages. Frequently, a website may be associated with a single domain name, although some websites may potentially encompass more than one domain name. The concepts described herein may be applied on a per-website basis. Alternatively, in some implementations, the concepts described herein may be applied on a per-webpage basis.

While servers 110-140 are shown as separate entities, it may be possible for one or more servers 110-140 to perform one or more of the functions of another one or more of servers 110-140. For example, it may be possible that two or more of servers 110-140 are implemented as a single server. It may also be possible for one of servers 110-140 to be implemented as multiple, possibly distributed, computing devices.

Network 150 may include one or more networks of any kind, including, but not limited to, a local area network (LAN), a wide area network (WAN), metropolitan area networks (MAN), a telephone network, such as the Public Switched Telephone Network (PSTN), an intranet, the Internet, a memory device, another type of network, or a combination of networks.

Although FIG. 1 shows example components of environment 100, in other implementations, environment 100 may contain fewer components, different components, differently arranged components, and/or additional components than those depicted in FIG. 1. Alternatively, or additionally, one or more components of environment 100 may perform one or more other tasks described as being performed by one or more other components of environment 200.

Figure 2:
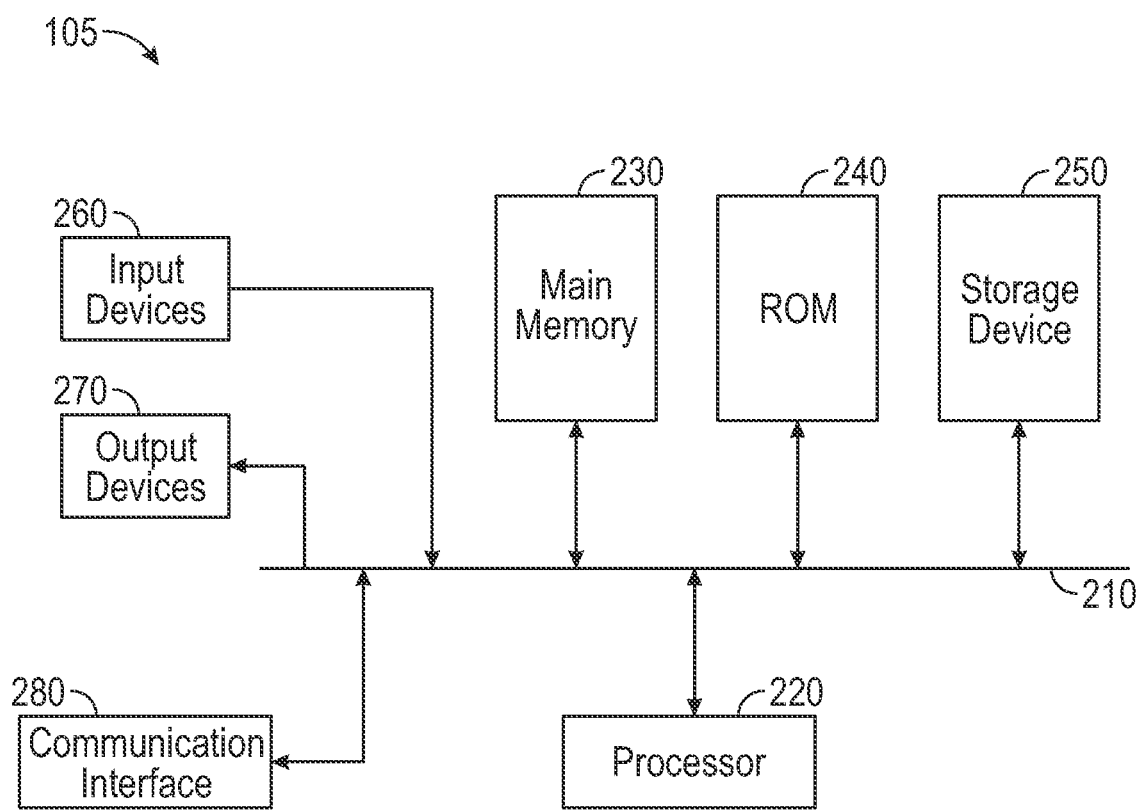
FIG. 2 is an exemplary diagram of a client of FIG. 1 according to an implementation consistent with the principles of the present disclosure.

FIG. 2 is an exemplary diagram of a user/client 105 or server entity (hereinafter called "client/server entity"), which may correspond to one or more of the clients and servers, according to an implementation consistent with the principles of the invention. The client/server entity 105 may include a bus 210, a processor 220, a main memory 230, a read only memory (ROM) 240, a storage device 250, one or more input devices 260, one or more output devices 270, and a communication interface 280. Bus 210 may include one or more conductors that permit communication among the components of the client/server entity 105.

Processor 220 may include any type of conventional processor or microprocessor that interprets and executes instructions. Main memory 230 may include a random access memory (RAM) or another type of dynamic storage device that stores information and instructions for execution by processor 220. ROM 240 may include a conventional ROM device or another type of static storage device that stores static information and instructions for use by processor 220. Storage device 250 may include a magnetic and/or optical recording medium and its corresponding drive.

Input device(s) 260 may include one or more conventional mechanisms that permit an operator to input information to the client/server entity 105, such as a scanner, phone, camera, scanning device, keyboard, a mouse, a pen, voice recognition and/or biometric mechanisms, etc. Output device(s) 270 may include one or more conventional mechanisms that output information to the operator, including a display, a printer, a speaker, an alarm, a projector, etc. Communication interface 280 may include any transceiver-like mechanism that enables the client/server entity 105 to communicate with other devices 105 and/or systems. For example, communication interface 280 may include mechanisms for communicating with another device 105 or system via a network, such as network 150.

As will be described in detail below, the client/server entity 105, consistent with the principles of the invention, performs certain receiving, communicating, generating, output providing, correlating, and storing operations. The client/server entity 105 may perform these operations in response to processor 220 executing software instructions contained in a computer-readable medium, such as memory 230. A computer-readable medium may be defined as one or more physical or logical memory devices and/or carrier waves.

The software instructions may be read into memory 230 from another computer-readable medium, such as data storage device 250, or from another device via communication interface 280. Examples of computer-readable mediums include, but are not limited to, magnetic media such as hard disks, floppy disks, and magnetic tape; optical media such as CD ROM discs and DVDs; magneto-optical media such as optical discs; and hardware devices that are specially configured to store and perform programming instructions, such as read-only memory (ROM), random access memory (RAM), flash memory, and the like. The software instructions contained in memory 230 causes processor 220 to perform processes that will be described later. Alternatively, hardwired circuitry may be used in place of or in combination with software instructions to implement processes consistent with the principles of the invention. Thus, implementations consistent with the principles of the invention are not limited to any specific combination of hardware circuitry and software.

Figure 3:
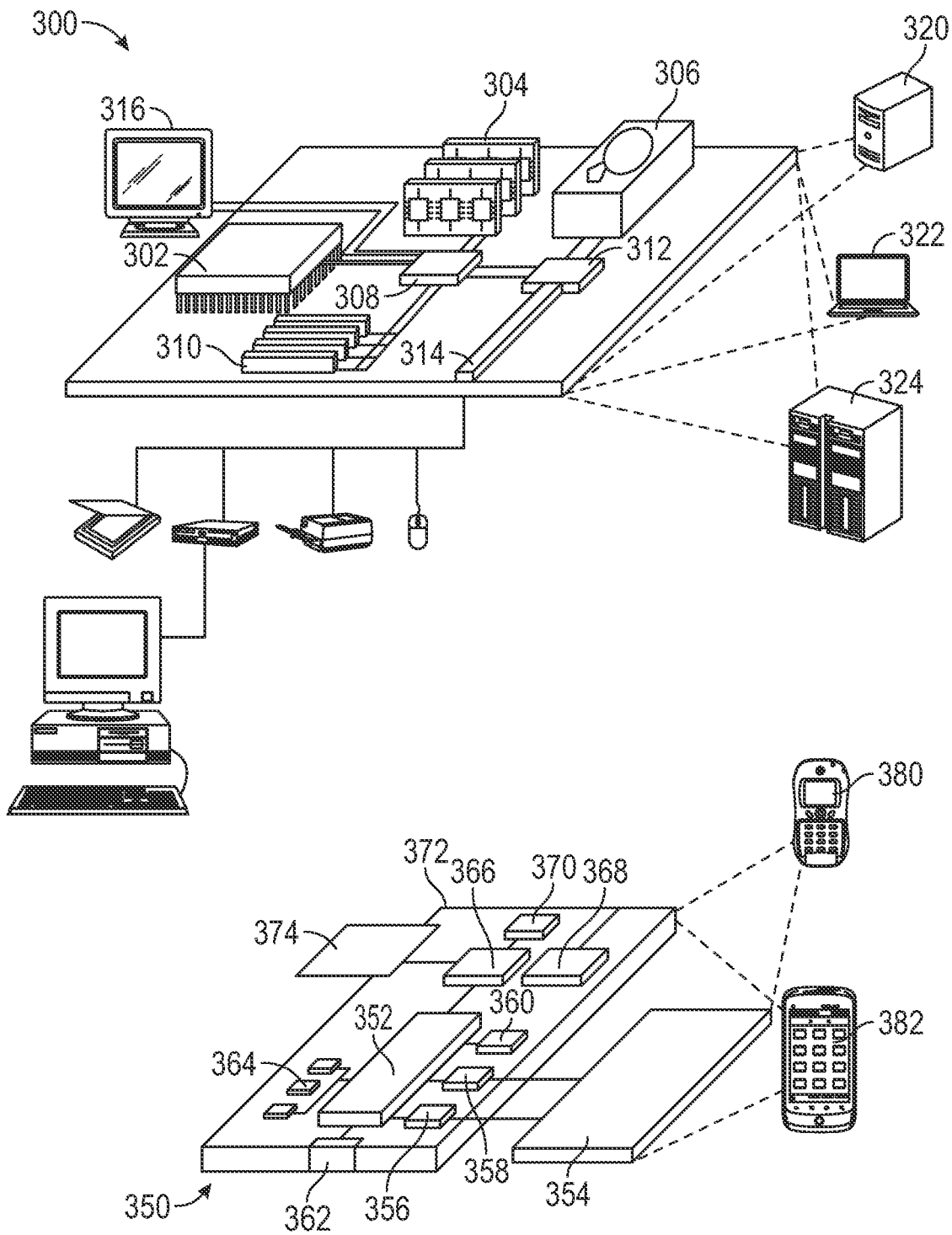
FIG. 3 is a diagram of an example computing device and mobile computing device.

FIG. 3 is a diagram of an example of a computing device 300 and a mobile computing device 350, which may be used with the techniques described here. Computing device 300 or mobile computing device 350 may correspond to, for example, a client 105 and or a server 110-140. Computing device 300 is intended to represent various forms of digital computers, such as laptops, desktops, workstations, personal digital assistants, servers, mainframes, and other appropriate computers. Mobile computing device 350 is intended to represent various forms of mobile devices, such as scanners, scanning devices, personal digital assistants, cellular telephones, smart phones, tablet computers, and other similar computing devices. The components show in FIG. 3, their connections and relationships, and their functions, are meant to be examples only, and are not meant to limit implementations described herein.

Computing device 300 may include a processor 302, a memory 304, a storage device 306, a high-speed interface 308 connecting to a memory 304 and high-speed expansion ports 310, and a low-speed interface 312 connecting to a low-speed expansion port 314 and a storage device 306. Each of components 302, 304, 306, 308, 310, 312, and 314 are interconnected using various buses, and may be mounted on a common motherboard or in other manners as appropriate. Processor 302 can process instructions for execution within computing device 300, including instructions stored in memory 304 or on storage device 306 to display graphical information for a graphical user interface (GUI) on an external input/output device, such as display 316 coupled to high-speed interface 308. In other implementations, multiple processors and/or multiple buses may be used, as appropriate, along with multiple memories and types of memory. Also, multiple computing devices 300 may be connected, with each device providing portions of the necessary operations, as a server bank, a group of blade servers, or a multi-processor system, etc.

Memory 304 stores information within computing device 300. In some implementations, memory 304 includes a volatile memory unit or units. In another implementation, memory 304 may include a non-volatile memory unit or units. Memory 304 may also be another form of computer-readable medium, such as a magnetic or optical disk. A computer-readable medium may refer to a non-transitory memory device. A memory device may refer to storage space within a single storage device or spread across multiple storage devices.

Storage device 306 is capable of providing mass storage for computing device 300. In some implementations, storage device 306 may be or contain a computer-readable medium, such as a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described herein. The information carrier is a computer or machine-readable medium, such as memory 304, storage device 306, or a memory on processor 302.

High-speed interface 308 manages bandwidth-intensive operations for computing device 300, while low-speed interface 312 manages lower bandwidth-intensive operations. Such allocation of functions is an example only. In some implementations, high-speed interface 308 is coupled to memory 304, display 316, such as through a graphics processor or accelerator, and to high-speed expansion ports 310, which may accept various expansion cards. In this implementation, low-speed interface 312 may be coupled to storage device 306 and low-speed expansion port 314. Low-speed expansion port 314, which may include various communication ports, such as USB, Bluetooth, Ethernet, wireless Ethernet, etc., may be coupled to one or more input/output devices, such as a keyboard, a pointing device, a scanner, or a networking device such as switch or router, e.g., through a network adapter.

Computing device 300 may be implemented in a number of different forms, as shown in the figures. For example, computing device 300 may be implemented as a standard server 320, or in a group of such servers. Computing device 300 may also be implemented as part of a rack server system 324. In addition, computing device 300 may be implemented in a personal computer, such as a laptop computer 322. Alternatively, components from computing device 300 may be combined with other components in a mobile device, such as mobile computing device 350. Each of such devices may contain one or more computing devices 300, 350, and an entire system may be made up of multiple computing devices 300, 350 communicating with each other.

Mobile computing device 350 may include a processor 352, a memory 364, an input/output ("I/O") device, such as a display 354, a communication interface 366, and a transceiver 368, among other components. Mobile computing device 350 may also be provided with a storage device, such as a micro-drive or other device, to provide additional storage. Each of the components 352, 364, 354, 366, and 368 are interconnected using various buses, and several of the components may be mounted on a common motherboard or in other manners as appropriate.

Processor 352 can execute instructions within mobile computing device 350, including instructions stored in memory 364. Processor 352 may be implemented as a chipset of chips that include separate and multiple analog and digital processors. Processor 352 may provide, for example, for coordination of the other components of mobile computing device 350, such as control of user interfaces, applications run by mobile computing device 350, and wireless communication by mobile computing device 350.

Processor 352 may communicate with a user through control interface 358 and display interface 356 coupled to a display 354. Display 354 may be, for example, a TFT LCD (Thin-Film-Transistor Liquid Crystal Display) or an OLED (Organic Light Emitting Diode) display or other appropriate display technology. Display interface 356 may include appropriate circuitry for driving display 354 to present graphical and other information to a user. Control interface 358 may receive commands from a user and convert the commands for submission to processor 352. In addition, an external interface 362 may be provided in communication with processor 352, so as to enable near area communication of mobile computing device 350 with other devices. External interface 362 may provide, for example, for wired communications in some implementations, or for wireless communication in other implementations, and multiple interfaces may also be used.

Memory 364 stores information within mobile computing device 350. Memory 364 can be implemented as one or more of a computer-readable medium or media, a volatile memory unit or units, or a non-volatile memory unit or units. Expansion memory 374 may also be provided and connected to mobile computing device 350 through expansion interface 372, which may include, for example, a SIMM (Single In Line Memory Module) card interface. Such expansion memory 374 may provide extra storage space for device 350, or may also store applications or other information for mobile computing device 350. Specifically, expansion memory 374 may include instructions to carry out or supplement the processes described herein, and may include secure information also. Thus, for example, expansion memory 374 may be provided as a security module for mobile computing device 350, and may be programmed with instructions that permit secure use of mobile computing device 350. In addition, secure applications may be provided via the SIMM cards, along with additional information, such as placing identifying information on the SIMM card in a non-hackable manner.

Expansion memory 374 may include, for example, flash memory and/or NVRAM memory. In some implementations, a computer program product is tangibly embodied in an information carrier. The computer program product contains instructions that, when executed, perform one or more methods, such as those described herein. The information carrier is a computer-or machine readable-medium, such as memory 364, expansion memory 374, or a memory on processor 352, that may be received, for example, over transceiver 368 or external interface 362.

Mobile computing device 350 may communicate wirelessly through communication interface 366, which may include digital signal processing circuitry where necessary. Communication interface 366 may provide for communications under various modes or protocols, such as GSM voice calls, SMS, EMS or MMS messaging, CDMA, TDMA, PDC, WCDMA, CDMA2000, or GPRS, among others. Such communication may occur, for example, through transceiver 368. In addition, short-range communication may occur, such as using a Bluetooth, WiFi, or other such transceiver. In addition, GPS (Global Positioning System) received module 370 may provide additional navigation-and location-related wireless data to mobile computing device 350, which may be used as appropriate by applications running on mobile computing device 350.

Mobile computing device 350 may also communicate audibly using audio codec 360, which may receive spoken information from a user and covert the received spoken information to digital information. Audio codec 360 may likewise generate audible sound for a user, such as through a speaker, e.g., in a handset of mobile computing device 350. Such sound may include sound from voice telephone calls, may include recorded sound, such as voice messages, music files, etc., and may also include sound generated by applications operating on mobile computing device 350.

Mobile computing device 350 may be implemented in a number of different forms, as shown in the figure. For example, mobile computing device 350 may be implemented as a cellular telephone 380. Mobile computing device 350 may also be implemented as part of a smart phone 382, personal digital assistant, or other similar mobile devices.

Various implementations described herein can be realized in digital electronic circuitry, integrated circuitry, specially designed ASICs (application specific integrated circuits), computer hardware, firmware, software, and/or combinations thereof. These various implementations can include implementations in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs, also known as programs, software, software applications, or code, include machine instructions for a programmable processor, and can be implemented in a high-level procedural and/or object-oriented programming language, and/or in assembly/machine language. As used herein, the terms "machine-readable medium" and "computer-readable medium" refer to any apparatus and/or device, such as magnetic discs, optical disks, memory, Programmable Logic Devices ("PLDs"), used to provide machine instructions and/or data to a programmable processor, including a machine-readable medium that receives machine instructions as a machine-readable signal. The term "machine-readable signal" refers to any signal used to provide machine instructions and/or data to a programmable processor.

The contents of computer-readable medium may physically reside in one or more memory devices accessible by server. Computer-readable medium may include a database of entries corresponding to certain subject matter disclosed herein. A user or organization's information may be provided in information fields and stored in a database, as set forth herein. Said fields are customizable and may include additional or alternative fields based on the user's needs. Said information is accessible through the server.

To provide for interaction with a user, the techniques described herein can be implemented on a computer having a display device, such as a CRT (cathode ray tube), LCD (liquid crystal display), or LED (Light Emitting Diode) monitor, for displaying information to the user and a keyboard and a pointing device by which the user can provide input to the computer. Other kinds of devices can be used to provide for interaction with a user as well; for example, feedback provided to the user can be any form of sensory feedback, such as visual feedback, auditory feedback, or tactile feedback; and input from the user can be received in any form, including acoustic, speech, or tactile input.

Figure 4:
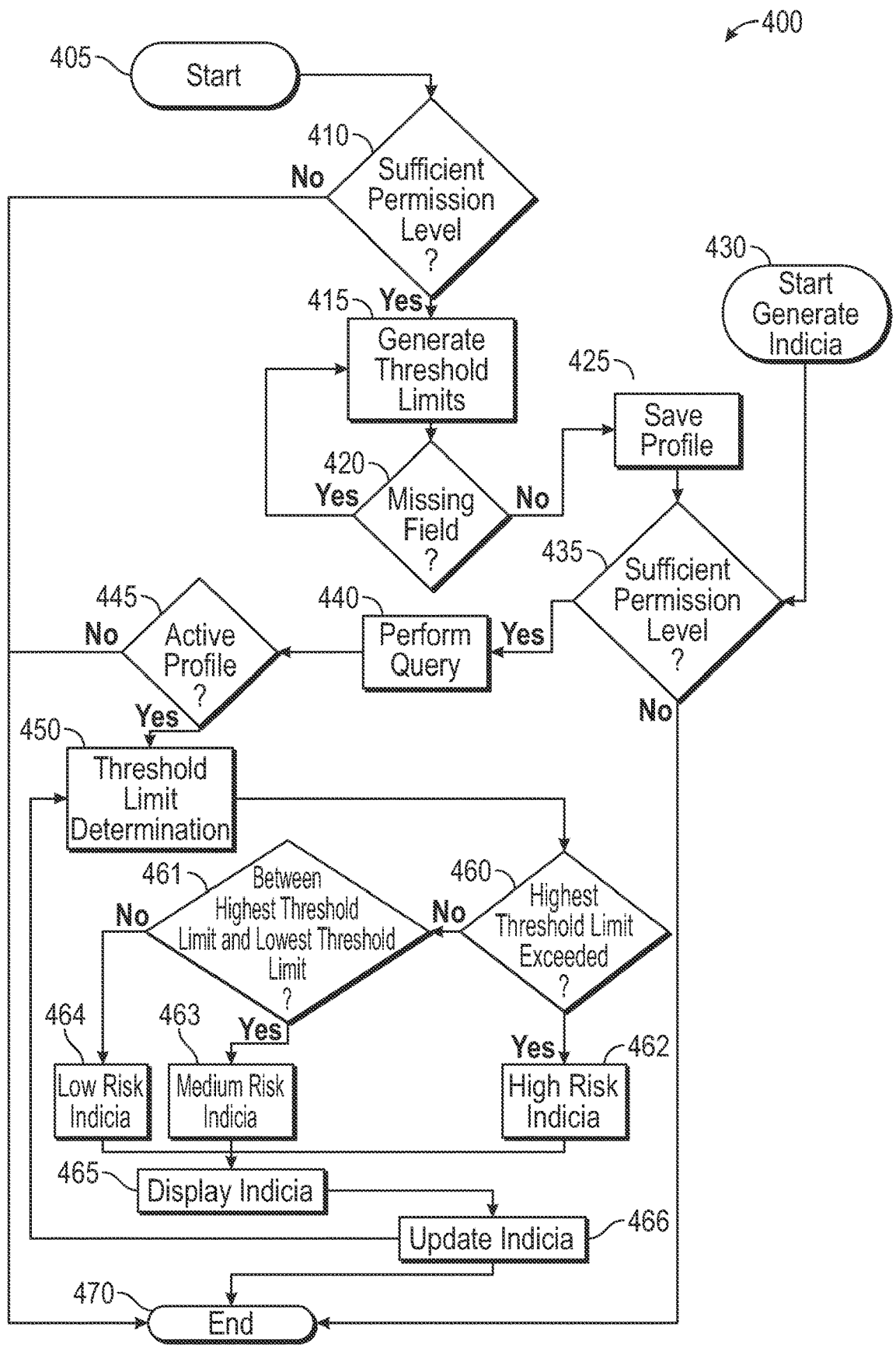
FIG. 4 is a flowchart illustrating certain method steps of a method for visually displaying instances of increased susceptibility for commission of medical errors.
Figure 5:
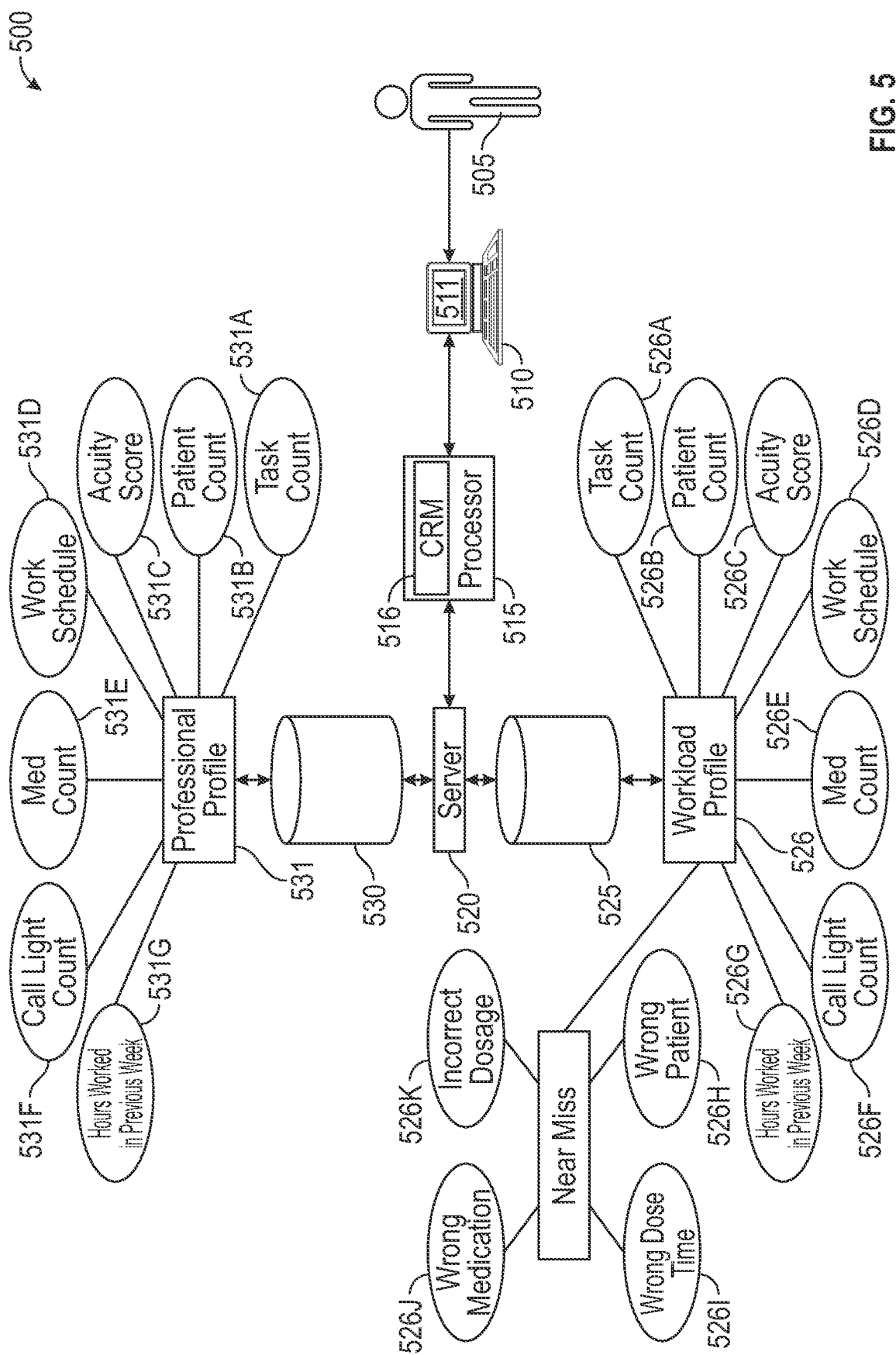
FIG. 5 is a diagram illustrating a system embodying features consistent with the principles of the present disclosure.

FIGS. 4 and 5 illustrate an embodiment of a method 400 and system 500, respectively, designed to assess whether a healthcare professional or team of healthcare professionals are subject to an increased level of risk for committing a medical error due to their experienced workload, or certain aspects thereof, and generate displayable indicia reflecting such assessment. Displayable indicia generated by the systems and methods of the present disclosure may be presented on the user interface of a computing device or other device having a visual display component to provide visually identifiable cues as to whether an individual's or team of individuals' experienced workload is likely to compromise that individual's or team of individuals' ability to provide optimal healthcare based on the individual's or team of individuals' work history. Applications of the systems and methods disclosed herein may be utilized for the assessment of and generation of displayable indicia for a single individual or multiple individuals. Thus, in one aspect, the systems and methods of the present disclosure are directed toward a risk assessment tool that may be readily implemented in hospitals or other healthcare environments and utilized by healthcare professionals to better identify instances where a healthcare professional or team of healthcare professionals requires assistance or a reduction in their workload to mitigate the likelihood of a medical error occurring. In some embodiments, one or more steps of the methods of the present disclosure may be reiterated in accordance with a defined time schedule to monitor changes in an individual or team of individual and provide updated indicia corresponding to the risks associated with such changes.

As shown in FIG. 5, the system 500 of the present disclosure comprises at least one non-transitory computer-readable medium 516 containing computer program instructions executable by at least one processor 515 to perform various method steps disclosed herein. Although the at least one non-transitory computer-readable medium 516 is sometimes referred to herein in singular form, i.e., "a non-transitory computer-readable medium" or "the non-transitory computer-readable medium," it is understood that a plurality of non-transitory computer-readable mediums may alternatively be used to achieve the described functionality or arrangement. Accordingly, in some embodiments, a plurality of non-transitory computer-readable mediums 516 may be used. The non-transitory computer-readable medium 516 may be coupled to a processor 515 in some embodiments, as shown in FIG. 5. Examples of the non-transitory computer-readable mediums 516 which may be utilized include, but are not limited to, magnetic media such as hard disk, floppy disks, and magnetic tape; optical media such as CD ROM discs and DVDSs; magneto-optical media such as optical discs; and hardware devices that are specifically configured to store and perform programming instructions, such as read-only memory (ROM), random access memory (RAM), flash memory, and the like. In some embodiments, the programming instructions may be divided into and stored as a plurality of modules within the non-transitory computer-readable medium 516.

To execute the program instructions within the non-transitory computer-readable medium 516, the system 500 may further comprise at least one processor 515 operably connected to the at least one non-transitory computer-readable medium 516. Although the at least one non-transitory computer-readable medium 516 is sometimes referred to herein in singular form, i.e., "a processor" or "the processor," it is understood that a plurality of processors may alternatively be used to achieve the described functionality or arrangement. Accordingly, in some embodiments, a plurality of processors 515 operably connected to one or more non-transitory computer-readable mediums 516 may be used. The processor 515 may be any processor or microprocessor suitable for executing the program instructions of the non-transitory computer-readable medium 516. In an embodiment, the processor 515 may be a component of a larger computing device having some or all of the feature of computing device 300 or mobile computing device 350. Accordingly, the inventive subject matter disclosed herein, in full or part, may be implemented or utilized in devices including, but not limited to, laptops, desktops, workstations, personal digital assistants, cellular telephones, tablet computers, or any other computing device having a processor suitable for executing the program instructions within the non-transitory computer-readable medium 516.

The processor 515 is operably connected to one or more data repositories in which information utilized or in certain method steps disclosed herein is stored and/or may be stored. Accordingly, in some embodiments, the system 500 of the present disclosure may further comprise one or more data repositories. In some embodiments, the processor 515 may be operably connected to the one or more data repositories via a server 520, as shown in FIG. 5. In other embodiments, the processor 515 may be directly connected to the one or more repositories via a wired or wireless connection. In some embodiments, the one or more repositories may include one or more relational databases adapted to store information in one or more tables, one or more object databases adapted to store information as objects, or combinations thereof.

Figure 8:
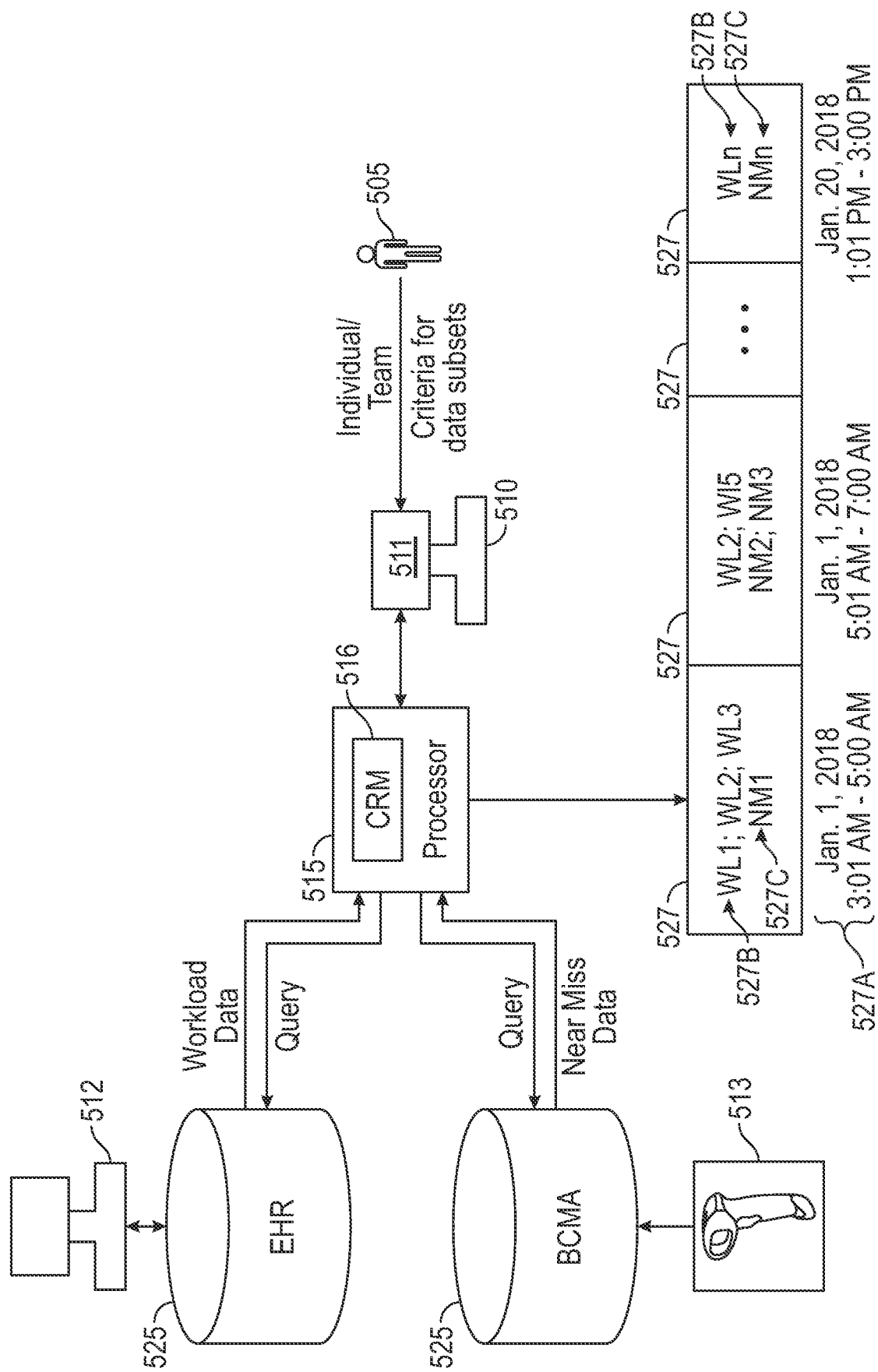
FIG. 8 is a diagram illustrating certain features of a system and method according to one embodiment consistent with the principles of the present disclosure.

In an embodiment, the processor 515 is operably connected to a first database 525 containing information relating to one or more healthcare professionals' work history over a defined period of time. Information within the first database 525 may include workload data that includes data corresponding to the work conditions experienced by one or more individuals over a defined period of their work history and near-miss data representing one or more instances of a near miss associated with the one or more individuals. As used herein, the term "near miss" and grammatical equivalents thereof are understood to mean an instance where an action, which if carried out would result in the occurrence of a medical error, was identified or stopped before giving rise to the occurrence of a medical error. In one embodiment, the first database 525 may comprise an electronic health record ("EHR") database, a Barcoded Medication Administration ("BCMA") database, or both, as shown in FIG. 8.

As shown in FIG. 5, the first database 525 may be configured to store a plurality of workload profiles 526 therein and the various workload and near-miss data associated with such profiles, wherein each workload profile corresponds to an individual healthcare professional. Workload data stored within the first database 525 may include data corresponding to a variety of environmental working conditions experienced by one or more individuals during a defined period of time including, but not limited to, task count data 526A, patient count data 526B, acuity score data 526C, work schedule data 526D, medication count data 526E, call light count data 526F, and hours worked in the previous week data 526G. Task count data 526A corresponds to the total number of tasks an individual is scheduled to perform or has performed at a specific time or time interval. Patient count data 526B corresponds to the total number of patients an individual is or was assigned at a specific time or time interval. Acuity score data 526C corresponds to an individual's total patient acuity level. In some embodiments, the total patient acuity level may be based on patient vital signs, patient alertness, and the presence of oxygen support, though additional or alternative patient physiological, mental, or other medical factors may define, in whole or in part, total patient acuity level. Work schedule data 526D corresponds to the date and time an individual is scheduled or was scheduled to work at a specific time or time interval. Medication count data 526E corresponds to the total amount of medication tasks that an individual must perform at a specific time or time interval. Call light count data 526F corresponds to the total number of times an individual has been required to assist patients at a specific time or time interval due to patient request. Hours worked in the previous week data 526G corresponds to how many hours in excess of forty hours an individual is scheduled to work or has worked at a specific time or time interval. In some embodiments, workload data within the first database 525 may further include healthcare professional assessment data corresponding to survey information, including, but not limited to, known medical conditions of an individual, medications taken by the individual, the individual's state of mind, and information provided by other individuals about the individual.

In an embodiment, workload data 526A-526G may comprise data retrieved from one or more databases associated with a hospital or other medical facility's EHR system. Workload data within the one or more databases associated with an EHR system may be generated and/or transmitted to an EHR database, at least in part, using one or more computing devices 510, 512 and/or other devices, such as barcode or radio frequency identification ("RFID") readers, or systems configured to log, generate, receive input from users, or transmit information related to the working conditions 526A-526G of an individual's workload. Accordingly, in embodiments wherein the first database 525 includes an EHR database, the system 500 of the present disclosure may further comprise one or more computing devices 510, 512 and/or other devices or systems configured to log, generate, or transmit information related to the working conditions 526A-526G of an individual's workload operably connected to the first database 525, as shown in FIG. 8.

Near-miss data stored within the first database 525 includes data representing actions or action types resulting in the occurrence of a near miss. Such data may include, but is not limited to, wrong patient data 526H, wrong dose time data 526I, wrong medication data 526J, and incorrect dosage data 526K. Wrong patient data corresponds to instances where a near miss occurred due to an individual attempting to perform a medication-based task on a patient other than the patient to which such medication-based task was actually assigned. Wrong dose time data 526I corresponds to instances where a near miss occurred due to an individual attempting to perform a medication-based task at a different time than the time in which such medication-based task was actually scheduled. Wrong medication data 526J corresponds to instances where a near miss occurred due to an individual attempting to give a patient a medication that differs from the medication actually prescribed. Incorrect dosage data 526K corresponds to instances where a near miss occurred due to an individual attempting to administer a dosage of medication differing from the dosage actually prescribed. In some embodiments, wrong patient data 526H, wrong dosage time data 526I, wrong medication data 526J, and wrong dosage data 526K may also include data corresponding to instances where an individual has made a mistake that is not identified or cured prior to the occurrence of a medical error or instances where an individual incorrectly overrides systems and/or protocols designed to prevent medical errors.

In some embodiments, near-miss data 526H-526K may comprise data retrieved from a BCMA system, which generates data related to the distribution of prescription medications in response to the scanning of barcodes associated with patients and medications and identifies instances where a selected medication should not be administered to a target patient based on such scanned information, or one or more databases associated therewith. Thus, in an embodiment, near-miss data 526H-526K data may be generated, at least in part, by scanning a plurality of barcodes assigned to various medications and patients over a period of time using a barcode reader 513. Accordingly, in embodiments wherein the first database 525 includes a BCMA database, the system 500 of the present disclosure may further comprise one or more barcode readers 513 operably connected to the first database 525, as shown in FIG. 8.

In an embodiment, the first database 525 may further store threshold limit data containing a plurality of threshold limits, wherein each threshold limit represents a quantitative threshold corresponding to the amount of a specific working condition that a specific individual can tolerate before being subject to an increased risk for committing a medical error. Threshold data may include threshold limits corresponding to the task count 531A, patient count 531B, acuity score 531C, work schedule 531D, mediation count 531E, call light count 531F, hours worked in the previous week 531G an individual can tolerate within their workload before being subject to an increased risk of committing a medical error. In embodiments where the threshold limit data is stored within the first database 525, each threshold limit may be associated with a workload profile 526. In some embodiments, threshold data utilized by the system 500 and methods of the present disclosure may be stored in a second database 530 that is operably connected to the processor 515. In such embodiments, the second database 530 may be configured to store, and the threshold limit data may be associated with, a plurality of professional profiles 531 therein, where each professional profile corresponds to an individual healthcare professional.

Displayable indicia generated by the processor's 515 execution of the program instructions within the computer-readable medium 516 may be displayed on the user interface 511 of one or more computing devices 510 operably connected to the processor 515. Accordingly, in some embodiments, the system 500 may further comprise one or more computing devices 510 operably connected to the processor 515. In addition to displaying indicia, the one or more computing devices 510 and user interfaces 511 thereof may be utilized by users 505 to instruct the processor 515 to input data into or retrieve data from the system's 500 one or more data repositories in some embodiments. For instance, in some embodiments, the one or more computing devices 510 and user interface 511 may be utilized by users 505 to input and subsequently store information corresponding to a specific working condition experienced by an individual, to manually define or edit a threshold limits, and/or edit other information within or associated with the workload profiles 526 or professional profiles 531 within the system's 500 one or more data repositories. In some embodiments, the ability to input, retrieve, display, or otherwise access data generated by or contained within the systems and methods of the present disclosure may be limited based on user permission levels 600.

FIG. 4 provides a flow chart 400 illustrating certain method steps that may be executed to carry out a computer implemented method for visually displaying instances of increased susceptibility for commission of medical errors in accordance with one embodiment of the present disclosure. Step 405, indicates the beginning of the method. In some embodiments, the method of the present disclosure may include one or more user-verification steps 410, 435 before subsequent steps of the method may be executed or certain information or features of the system of the present disclosure may be accessed. In one such embodiment, users 505 may be required to provide information, via the user interface 511 of the one or more computers 510, for verification by the processor 515 to ensure users 505 have sufficient credentials to initiate threshold limit generation step 415. In instances where the information inputted by a user 505 cannot be verified by the processor 515 or the inputted information otherwise does not correspond to an individual having a sufficient permission level to initiate threshold limitation generation step 415, the user 505 is denied access. In some embodiments, the system and method of the present disclosure may proceed to end step 470 in the event a user 505 is denied access for having an insufficient permission level. Conversely, if the information inputted by a user 505 is verified by the processor 515 to correspond to an individual having a sufficient permission level, the method may proceed to threshold limit generation step 415 in which threshold limits are defined for each distinct working condition 526A-526G within the workload data.

Figure 7:
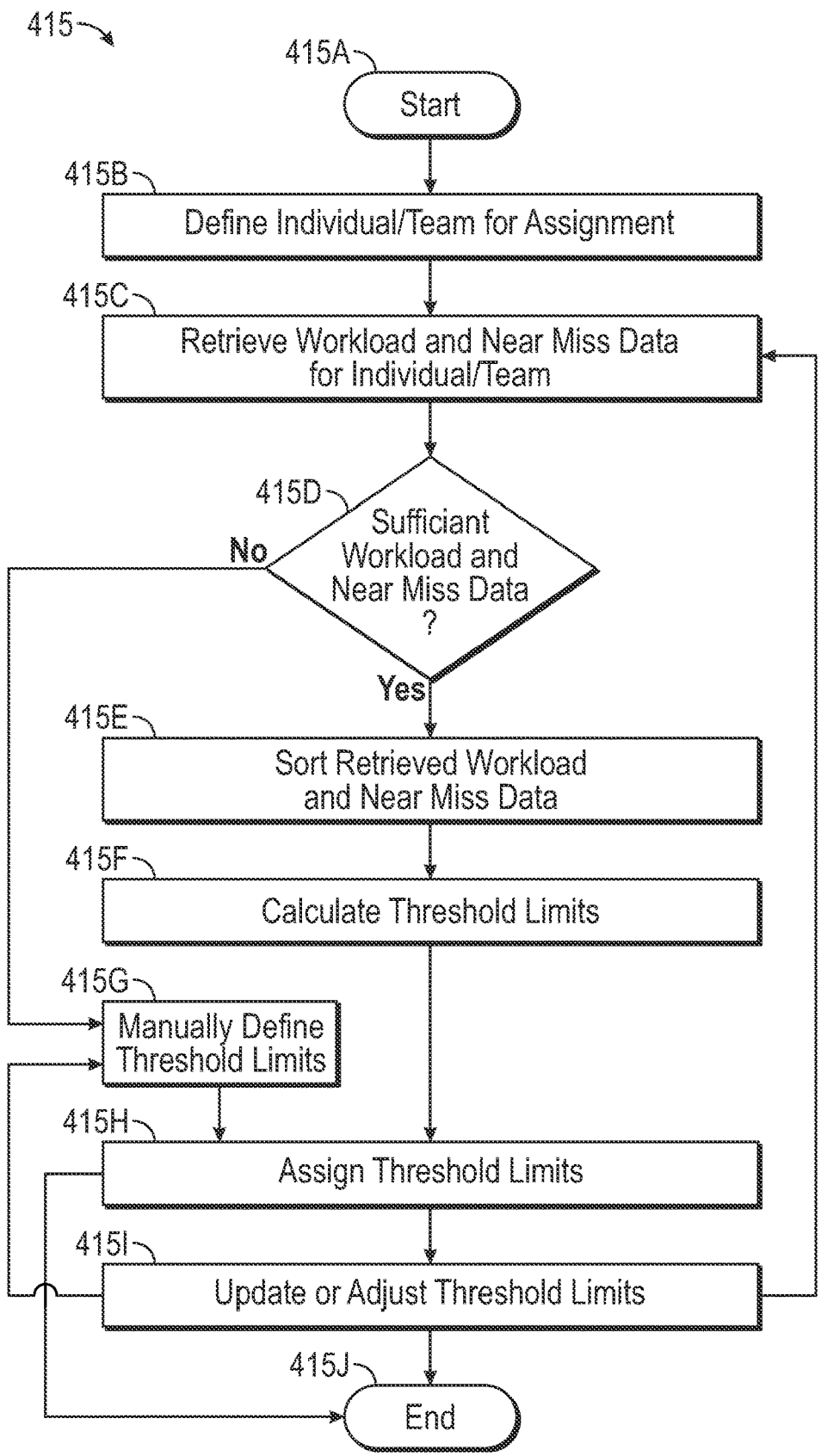
FIG. 7 is a flowchart illustrating certain method steps of a method for generating threshold limits according to one embodiment consistent with the principles of the present disclosure.

FIG. 7 shows a flowchart illustrating method steps that may be executed to carry out generate threshold limit determination step 415 in accordance within one embodiment of the present disclosure. Step 415A indicates the beginning of threshold limit determination step 415. The first step in threshold limit generation step 415 is to define the individual or team of individuals for which threshold limits are to be generated and assigned in step 415B. In an embodiment, users 505 may define the individual or team of individuals for which threshold limits are to be generated by interacting with and submitting individual or team information to the user interface 511 of the one or more computers 510 operably connected to the processor 515. In some embodiments, step 415B may include users 505 electing to create a new professional profile 531. When a user 505 chooses to create a new professional profile 531, the user may be prompted by the user interface 511 to provide a title for the professional profile 531 identifying the individual or team of individuals to which the professional profile 531 will correspond. The individual or team information submitted in step 415B is used by the processor 515 to create one or more database queries, which are submitted by the processor 515 to the system's 500 one or more repositories to retrieve workload and near-miss data for the defined individual or team of individuals in data retrieval step 415C, as shown in FIG. 8. In one embodiment, the database queries may be structure query language ("SQL") queries.

In some embodiments, the workload data and near-miss data retrieved in step 415C may be limited to workload and near-miss data corresponding to a defined period of time. For instance, in an embodiment, the workload and near-miss data retrieved in step 415C may include only workload and near-miss data corresponding to those working conditions experienced by and the near misses associated with an individual or team of individuals occurring during the 60 days prior to the time in which the one or more database queries are prepared by the processor 515 or transmitted to the system's 500 one or more data repositories. In an embodiment, the time period to which workload and near-miss data must correspond to be retrieve in step 415C may be user-specified. In such embodiments, step 415B may further include users 505 submitting or selecting a period of time in which workload and near-miss data must correspond to be retrieved in step 415C. In some embodiments, step 415B may include prompting users 505, via the user interface 511, to specify a period of time in terms of minutes, hours, days, years, duration of an individual's career, or combinations thereof. The period of time specified by the user 505 is used by the processor 515 in conjunction with the individual or team information to create the one or more database queries.

In one embodiment, the processor 515 may analyze the retrieved workload and near-miss data in step 415D to determine whether sufficient workload and near-miss data was retrieved for the individual or each individual within the team of individuals defined by the user 505 in step 415B. If sufficient workload and near-miss data is recovered, the method proceeds to either step 415E or 415F. In the event the processor 515 determines that workload and near-miss data was either not retrieved or retrieved in an insufficient amount to perform threshold calculation step 415F, the method may proceed step 415G and prompt users 505, via the user interface 511 of the one or more computing devices 510, to manually define one or more threshold limits 531A-531G for each individual for which the processor 515 determines insufficient workload and near-miss data was gathered. In some embodiments, during threshold limit generation step 415, users 505 may have the option to elect to manually input threshold limits 531A-531G after step 415B, regardless of whether sufficient workload and near-miss data exists for the individual or team of individuals. Upon a user 505 electing to manually define threshold limits 531A-531G, threshold limitation generation step 415 may proceed to step 415G after step 415B.

In an embodiment, the workload and near-miss data retrieved in step 415C corresponding to the individual or team of individuals defined in step 415B may be sorted and grouped into a plurality of data subsets 527 in step 415E in accordance with defined sorting criteria prior to threshold calculation step 415F. In instances where a team of individuals is defined in step 415B, the workload and near-miss data retrieved in step 415C may be sorted for each individual within the team, the team as a collective, or both the collective team and each individual within the team. Sorting criteria utilized in step 415E may be specified by users 505, as shown in FIG. 8, or preprogrammed. In some embodiments, retrieved workload and near-miss data may be stored and grouped into data subsets 527 based on the time interval 527A in which each working condition within the retrieved workload data and near miss within the retrieved near-miss data occurred, as shown in FIG. 8. In the example shown in FIG. 8, the working conditions experienced by and near misses associated with the individual or team of individuals defined in step 415B are sorted and grouped together based on time intervals 527A of approximately two hours such that all working conditions 527B and all near misses 527C occurring during a two-hour time period are grouped together within a data subset 527. It is understood, however, that the example provided in FIG. 8 is meant to illustrate but one embodiment in which data retrieved in step 415C may be subsequently sorted and that such data may be sorted and grouped together based on other sorting criteria including, but not limited to, longer time intervals, shorter time intervals, type of working condition, type of near miss, etc. In some embodiments, step 415E may be carried out prior to execution of step 415C so that the workload data and near-miss data corresponding to the individual or team of individuals defined in step 415B is sorted and grouped prior to retrieval in step 415C. In other embodiments, the threshold limit calculation step 415F may be carried out without the workload and near-miss data retrieved in 415C being sorted or grouped.

In threshold limit calculation step 415F, a threshold limit 531A-531G is calculated for each distinct working condition 526A-526G within the retrieved workload data for the individual or team of individuals defined in step 415B. In instances where a team of individuals is defined in step 415B, threshold limits 531A-531G may be calculated for each individual within the team, the team as a collective, or both the collective team and each individual within the team. To calculate the threshold limits 531A-531G for each distinct working condition 526A-526G represented in the workload data retrieved, the processor 515 may perform one or more regression analyses using the retrieved workload and near-miss data corresponding to the individual or team of individuals defined in step 415B to determine which, if any, of the working conditions experienced by the individual or team of individuals significantly increases their chance of committing a medical error or near miss. In some embodiments, the processor 515 may complete two regression analyses. In one such embodiment, a first regression analysis comparing each working condition to the presence of a near-miss within the near-miss data and a second regression analysis comparing each working condition to the to the total number of near misses within the near-miss data may be carried out by the processor 515. In instances where the retrieved workload a near-miss data is sorted and grouped into a plurality of subsets, the first regression analysis may include comparing each working condition 527B within a subset 527 to each near miss 527C within that subset 527 to determine which working conditions 527B within the subset 527 were significant to the occurrence of each respective near miss 527C. The foregoing process may be repeated by the processor 515 for each sorted subset 527. In an embodiment, working conditions determined to have a p-value less than 0.05 during the one or more regression analyses may be determined significant by the processor 515.

In an embodiment, step 415F may include determining one or more threshold limits 531A-531G for each distinct working condition based, at least in part, on the amount or value in which a specific working condition 526A-526G and the quantitative value associated therewith (i.e., the number of tasks assigned, number of call light counts experienced, the acuity scores of patients cared for, etc.) was present in one or more specified percentages of the total number of near misses within the near-miss data. For example, one specific working condition may correspond to instances where the individual or team of individuals assigned in step 415B was assigned ten tasks and a second specific working condition may correspond to instances where the individual or team of individuals was assigned five tasks. Thus, each working condition type or category (task count, patient count, acuity score, work schedule, med count, call light count, hours worked in the previous week) may have a plurality of specific instances, of the working condition represented within the data retrieved in step 415C and subsequently analyzed in step 415F.

In one embodiment, two threshold limits 531A-531G may be determined for each distinct working condition 526A-526G. The first and second threshold limit correspond to a first and second specified percentage, respectively, in which a specific working condition was present in the total number of near misses recorded within the near-miss data. The first threshold limit of each working condition corresponds to an amount of the working condition (the number or patients, tasks, medicine count, call light count, etc.) which, if reached or exceeded, would place the individual or team of individuals at what is considered to be a medium risk for committing a medical error or near miss. The second threshold limit corresponds to an amount of the same working condition which, if reached or exceeded, would place the individual or team of individuals at an increased risk of committing a medical error. For instance, in an embodiment, the first specified percentage may be set to 20% of the total near misses and the second specified percentage may be set to 25% of the total near misses. Using the foregoing example, if the near-miss data comprises 100 total near misses associated with the individual or team of individuals and in 20 of the near misses the individual or team of individuals was caring for six patients and in 25 of the near misses the individual or team of individuals was caring for eight patients, the processor 515 would determine the first threshold limit for patient count 531B is six and the second threshold limit for patient count 531B is eight.

It is understood that the specified percentages in the above example are for explanatory purposes only and that the one or more specified percentages may vary depending on the intended application for which the systems and methods of the present disclosure are being used. In determining which values or amounts of an experienced working condition within the workload data satisfies the one or more specified percentages of occurrence within the total near misses, the processor 515 may calculate the ratio of the number of near misses in which such amount or value of the working condition was present and the total number of near misses within the near-miss data. In instances where multiple amounts or values satisfy the one or more specified percentages, the processor 515 may, in some embodiments, select the smallest of the qualifying amounts or values to act as the threshold limit.

The one or more threshold limits 531A-531G determined in step 415F are subsequently assigned by the processor 515 to the defined individual or the team of individuals in step 415H. In an embodiment, step 415 may include assigning the one or more threshold limits 531A-531G to at least one of a corresponding professional profile 531 or workload profile 526 within the system's 500 one or more data repositories. In some embodiments, the one or more threshold limits 531A-531G determined in step 415F may be stored within the non-transitory computer-readable medium 516 or other local memory for quick access and subsequent use by the processor 515.

As shown in FIG. 7, in some embodiments, the threshold limit generation step 415 may further comprise updating or adjusting the one or more threshold limits 531-531G in step 415I. The one or more threshold limits 531A-531G of the individual or team of individuals defined in step 415B may be updated or adjusted to reflect new or different workload and near-miss data automatically by reiterating steps 415C-415H or manually by individuals having sufficient permission levels 600 to do so. Preferably, only users 505 having a managerial role 615 or system roles 620 may manually adjust or update the threshold limits 531A-531G. In some embodiments, the processor 515 may reiterate steps 415C-415F and 415H in accordance with a defined time schedule. In an embodiment, the time schedule may be such that the processor 515 reiterates steps 415C-415F and 415H every 60 days, though it is understood that the time schedule may be adjusted to cause the processor 515 to reiterate these steps more frequently (e.g., every 30 days, every week, every day, every hour, etc.) or less frequently (e.g., once every 90 days or once a year) depending on the intended application. In some embodiments, updates or adjustments to the one or more threshold limits 531A-531G may be carried out on a rolling historical basis, meaning the one or more threshold limits 531A-531G may be adjusted or updated a plurality of times every day, hour, or minute to account for the individual or team of individuals workload capacity in substantially real time. In one such embodiment, the processor 515 may reiterate steps 415C-415F and 415H every two minutes. Step 415J indicates the end of generate threshold limit step 415.

The threshold limits 531A-531G generated and assigned to an individual or team of individuals by the systems and methods of the present disclosure effectively provide quantitative values representing the amount of a specific working condition an individual or team of individuals can tolerate before being subject to an increased risk of committing a medical error. Accordingly, the threshold limits 431A-431G may be utilized by healthcare administrators and management to better understand the strengths and weaknesses of their staff and subsequently schedule staff, assign patients, and assign tasks in such a way that each staff member's strength is utilized while their weaknesses are mitigated to provide a safer, more efficient healthcare environment.

Once all threshold limits 531A-531G are generated and assigned to a workload profile 526 or professional profile 531 corresponding to the individual or team of individuals defined in step 415B, the profile to which the threshold limits 531A-531G are assigned may be saved in step 425 so that the threshold limits 531A-531G are tied to, contained within, or otherwise associated with the profile. Step 425 may be carried out automatically by the processor 515 following step 415 or 420 or may carried out manually by a user 505 by interacting with the user interface 511 of the one or more computing devices 510.

In some embodiments, following threshold limit generation step 415 and prior to save profile step 425, a missing field check 420 may be performed. In step 420, the processor 515 may analyze the workload profile 526 or professional profile 531 to which the generated threshold limits 531A-531G were assigned to ensure that the individual or team of individuals defined in step 415B have at least one threshold limit corresponding to each of the distinct types or categories of working conditions 526A-526G represented within the workload data. In the event the processor 515 determines that one or more threshold limits are missing, the processor 515 may prompt users 505, via the user interface 511 of the one or more computing devices 510, to manually define and input the missing threshold limits via the user interface 511. When manually defining and inputting the threshold limits, certain fields may be required. To ensure that all required fields are provided, the processor 515 may review the information input by a user 505 to ensure all required fields have been provided. If all required fields have been inputted, the inputted information is assigned to the individual or team of individuals and the method proceeds to step 425. If a user 505 fails to provide one or more required fields, the processor 515 may cause the user interface 511 to prompt the user 505 to input the missing fields. In some embodiments, the processor 515 may analyze other, non-threshold-limit, fields of the professional profiles 531 and/or workload profiles 526 within the system's 500 one or more data repositories to ensure that all fields deemed necessary are provided with information and prompt users 505, via the user interface 511 of the one or more computing devices 510, to provide such information if it is absent.

Once threshold limits 531A-531G have been assigned and saved to the professional profiles 531 and/or the workload profile 526 corresponding to the individual or group of individuals defined in step 415B, method 400 may proceed to start generate indicia step 430. As shown in FIG. 4, once threshold limits 431A-431G have been set for an intended individual or team of individuals, subsequent iterations of the method 400 of the present disclosure may begin at start generate indicia step 430. In some embodiments, users 505 may initiate the processor 515 to execute one or more method steps responsible for the generation of displayable indicia 462-464 indicative of individual's or team of individuals' susceptibility for committing a medical error due to their experienced workload by interacting with the user interface 511 of the one or more computing devices 510. In such embodiments, users 505 may be subject to a second user-verification step 435. In step 435, users 505 may be required to provide information, via the user interface 511 of the one or more computers 510, for verification by the processor 515 to ensure users 505 have sufficient credentials to initiate the processor 515 to execute the method steps which result in the generation of displayable indicia 462-464. In instances where the information inputted by a user 505 cannot be verified by the processor 515 or the inputted information otherwise does not correspond to an individual having a sufficient permission level to initiate the processor 515, the user 505 is denied access. In some embodiments, the system and method of the present disclosure may proceed to end step 470 in the event a user 505 is denied access for having an insufficient permission level. Conversely, if the information inputted by a user 505 is verified by the processor 515 to correspond to an individual having a sufficient permission level, the user may proceed to initiate the processor 515 to execute the method steps responsible for generating displayable indicia 462-464. In other embodiments, the processor 515 may begin executing the steps responsible for generating displayable indicia 462-464 without being initialized to do so by a user 505.

In query step 440, the processor 515 performs a database query to retrieve information from the system's 500 one or more data repositories indicative of whether an individual healthcare professional or team of health care professionals is currently active. In an embodiment, the processor 515 may retrieve one or more pieces of workload data from the first database 525. In one such embodiment, the processor 515 may retrieve patient count data 526B corresponding to the time in which the query is made from the workload data for the individual or team of individuals and subsequently determine, in step 445, whether each individual to which the patient count data 526B corresponds is active based on the value within patient count data 526B. If the retrieved patient count data 526B is not null or equal to zero, the processor 515 considers the individual to be active.

In another embodiment, each workload profile 526 may have data associated therewith corresponding to log times in which the individual to which the workload profile 526 relates has completed or performed a task. In such embodiments, the processor 515 may retrieve such log time data for the individual or team of individuals corresponding to a period of time predating the time in which the query is made and subsequently, in step 445, determine whether each individual to which the log time data corresponds is active based on the values within such data. If the retrieved log data is not null or equal to zero, the processor 515 considers the individual to be active. For instance, in an embodiment, any workload profile 526 having a task with a log time within 30 minutes of the time in which the query to retrieve log time data is made may be considered by the processor 515 as active.

In some embodiments, the task count data 526A associated with each workload profile 526 may have log times associated therewith. In other embodiments, the processor 515 may retrieve work schedule data 526D corresponding to the time in which the query is made from the workload data for the individual or team of individuals and subsequently determine, in step 445, whether each individual to which the work schedule data 526 corresponds is active based on whether the individual is scheduled to work. If the retrieved work schedule 526D data is not null or equal to zero, the processor 515 may consider the individual to be active. In an embodiment, the systems and methods of the present disclosure may proceed to end step 470 in the event no individual is found to be active. In some embodiments, the processor 515 may determine that each individual or team of individuals is active by default so that threshold limit determination step 450 is carried out for all individuals having a workload profile 526 within the system's 500 one or more data repositories.

After determining which individuals are active, the processor 515 proceeds to threshold limit determination step

450. During threshold limit determination step 450, the processor 515 retrieves the workload data representing the work conditions 526A-526G experienced by the individuals determined to be active during a specified period of time. In one embodiment, the processor 515 may retrieve workload data corresponding to the working conditions 526A-526G currently experienced by each active individual at the time such retrieval is performed, i.e., the processor 515 retrieves workload data representing the current, real time working conditions 526A-526G experienced by the active individuals. To retrieve workload data in step 450, the processor 515 may prepare and submitted one or more database queries to the system's 500 one or more data repositories.

The time period in which workload data is retrieved in step 450 may differ from the time period in which workload data is retrieved in step 415. The time period in which workload data is retrieved in step 450 may, in some embodiments, be later than the time period in which workload data is retrieved in step 415. In an embodiment, the workload data retrieved in step 415 may correspond to working conditions experienced over a span of time (e.g., working conditions experienced over the course of hours, days, weeks, months, etc.) and the workload data retrieved in step 450 may correspond to working conditions experienced at a specified point in time (e.g., the working conditions experienced by an individual on Jan. 1, 2018 at 3:00 PM).

Upon retrieving the workload data corresponding to active users, the processor 515 subsequently compares each working condition 526A-526G within thin workload data for each active individual to the corresponding threshold limit 531A-531G for the individual. Based on the foregoing comparison, the processor 515 generates at least one displayable indicia 462-464 for display on a user interface 511 operably connected to the processor 515 indicating whether an active individual or team of active individuals is at an increased risk of committing a medical error due to their experienced workload. In an embodiment, the processor 515 may generate one or more displayable indicia for each distinct working condition within the workload data contained within the system's 500 one or more data repositories. In embodiments where each working condition 526A-526D has two corresponding threshold limits 531A-531G, such as a first threshold limit corresponding to a medium risk threshold and a second threshold limit corresponding to a high-risk threshold provided above, the data for each working condition 526A-526G retrieved in step 450 may be compared to a plurality of threshold limits.

As shown in FIG. 4, in an embodiment, each piece of working condition 526A-526G data retrieved in step 450 may first be compared against the highest threshold limit corresponding to the working condition in step 460 to determine whether an individual or team of individuals is at high risk for committing a medical error due to the tested working condition. If the value contained within a piece of the retrieved working condition 526A-526G data equals or is greater than the highest threshold limit for that working condition, the processor 515 may determine the individual or team of individuals is at a high risk of committing a medical error due to that aspect of their experienced workload and generate displayable indicia representing the same in step 462. If the value contained within the piece of working condition data falls below the highest threshold limit for that working condition, the piece of data may be subsequently compared against the next or remaining threshold limit for that working condition in step 461 to determine whether an individual or team of individuals is at a medium risk for committing a medical error due to the tested work condition. If the value contained within the piece of retrieved working condition 526A-526G equals or is greater than the medium risk threshold limit and below the highest threshold limit, the processor 515 may determine the individual or team of individuals is at a medium risk of committing a medical error due to that aspect of their experienced workload and generate displayable indicia representing the same in step 463. If the value contained within the piece of working condition data falls below the medium risk threshold for that working condition, then the processor 515 may determine the individual or team of individuals is at a low risk of committing a medical error due to that aspect of their experienced workload and generate displayable indicia representing the same in step 463. For instance, if the processor 515 retrieves a piece of working data in step 450 corresponding to patient count 526B and the value in such piece of data is six (indicating the individual to which such piece of data corresponds is caring for six patients at the time specified in step 450), the medium-risk threshold limit for patient count is seven, and the high-risk threshold limit for patient count is greater than 8, then the processor 515 will determine the individual is at a low risk of committing a medical error due to their experienced patient count and generate indicia representing low risk 464. If, instead, the value within the piece of data corresponding to patient count in the above example were seven or nine, the processor 515 would generate medium-risk indicia 463 and high-risk indicia 462, respectively.

Once each piece of working condition 526A-526G retrieved in step 450 is compared in the foregoing manner for each individual, the displayable indicia 462-464 generated by the processor 515 may be transmitted to and subsequently displayed on the user interface 511 of the one or more computing devices 510 operably connected to the processor 515 in step 465. Displayable indicia 462-464 generated by the processor 515 may comprise symbols, components of symbols, images, components of images, text, colors, shapes, combinations thereof, or any other suitable visual elements.

Figure 9A:
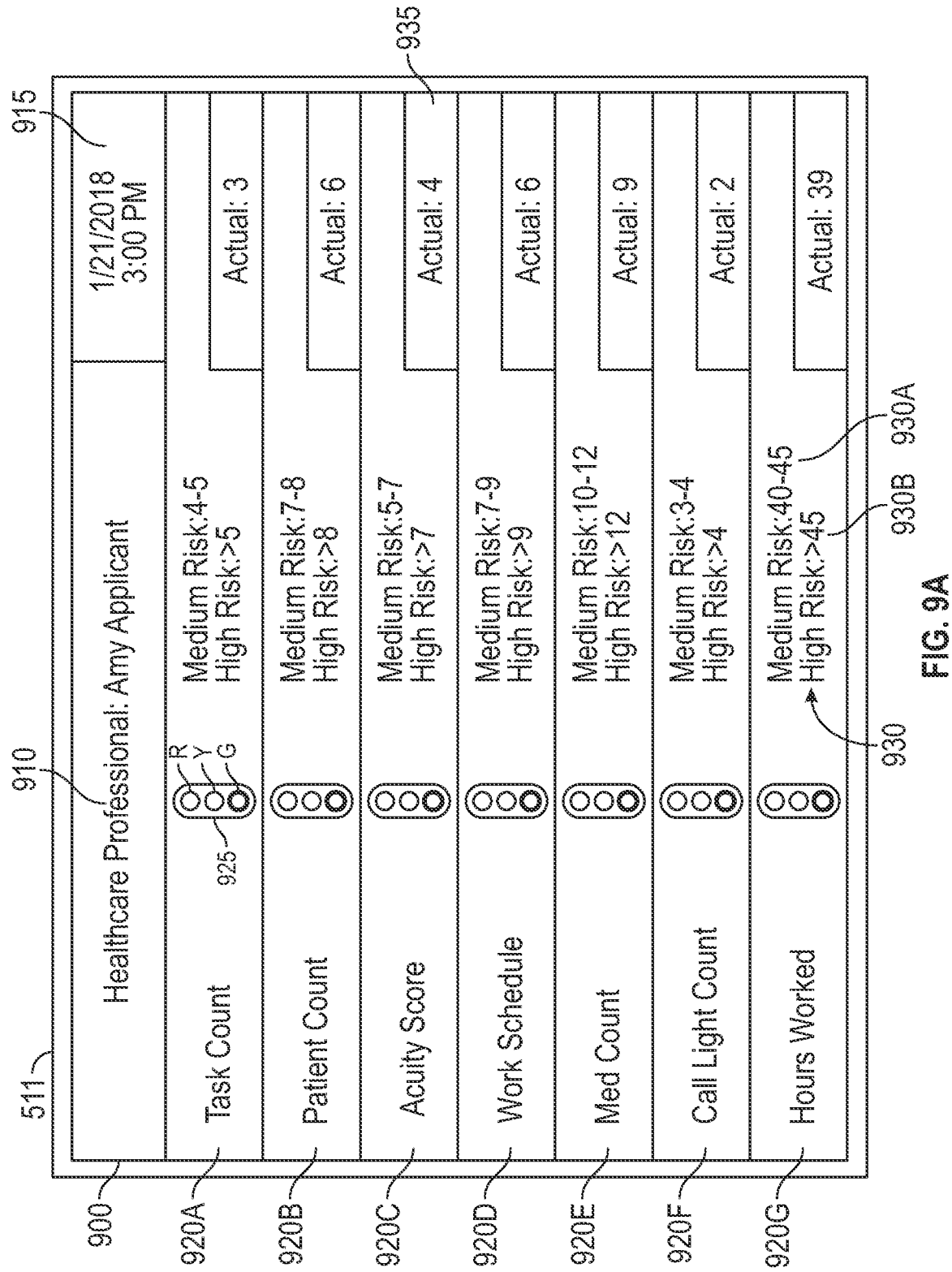
FIG. 9A shows a screen display presented on a user interface in accordance with one embodiment consistent with the principles of the present disclosure.
Figure 10:
FIG. 10 shows a screen display presented on a user interface in accordance with one embodiment consistent with the principles of the present disclosure.

In some embodiments, step 465 may include generating one or more screen displays containing the displayable indicia 462-464 generated by the processor 515. FIGS. 9A-10 each show a sample screen display 900, 1000 presented on a user interface 511.

As shown in FIGS. 9A-9B, display indicia step 465 may, in some embodiments, include generating and subsequently displaying one or more screen displays 900 containing information related to a single healthcare professional. As further shown in FIGS. 9A-9B, individual healthcare professional screen displays 900 may include one or more identification fields 910 containing information related to the individual to whom the screen display 900 relates, time fields 915 containing information related to the date and/or time to which the displayed information relates, and working condition fields 920A-920G.

In an embodiment, the screen displays 900 for individual healthcare professionals includes fields related to the individual's experienced task count 920, patient count 920B, acuity score 920C, work schedule 920D, med count 920E, call light count 920F, and hours worked in previous week 920G at the time in which the workload data in step 450 was retrieved or otherwise corresponds. In an embodiment, each working condition field 920A-920G may include one or more symbols 925 or other indicia indicating the level of increased risk the individual is subject to due to the working condition 526A-526G to which the working condition field 920A-920G corresponds. In an embodiment, the symbol 925 or other indicia for each working condition field 920A-920G may comprise a stoplight. In such embodiments, illumination (as indicated by bolded-line circle within drawings) of the red bulb R of the stoplight may correspond to the individual being at a high risk, the yellow bulb Y of the stoplight may correspond to the individual being at a medium risk, and the green bulb G may correspond to the individual being at a low risk of a committing a medical error due to the working condition 526A-526G to which the working condition field 920A-920G corresponds.

Each working condition field 920A-920G may further include information 930 concerning the one or more threshold limits corresponding to the working condition 526A-526G to which the working condition field 920A-920G corresponds. As shown in FIGS. 9A-9B, in some embodiments, information 930 concerning the one or more working conditions 526A-526G may include information pertaining to a first and second threshold limit 930A, 930B corresponding to the working condition 526A-526G to which the working condition field 920A-920G relates. Each working condition field 920A-920G may further include information 935 pertaining to the actual amount of the working condition 526A-526G experienced by the individual at the time in which the workload data in step 450 was retrieved or otherwise corresponds.

As shown in FIG. 10, display indicia step 465 may, in some embodiments, include generating and subsequently displaying one or more screen displays 1000 containing information related to a team of healthcare professionals. Such team screen displays 1000 may include one or more identification fields 1010 containing information relating to the healthcare team to which the screen display 1000 relates, time fields 1015 containing information related to date and/or time to which the displayed information relates, and individual healthcare professional fields 1020A-1020H, each containing information about the various individuals making up the healthcare team. In an embodiment, each individual healthcare professional field 1020A-1020H may include one or more symbols 1025 or other indicia indicating whether the individual to which the professional field 1020A-1020H corresponds is at an increased risk of committing a medical error due to one or more of the work conditions experienced by the individual at the time in which the workload data in step 450 was retrieved or otherwise corresponds. In some embodiments, the symbol 1025 or other indicia for each individual healthcare professional field 1020A-1020H may comprise a stoplight similar to that described above for the individual healthcare professional screen displays 900. Each individual healthcare professional field 1020A-1020G may further include a notes field 1030 in which information pertaining to the healthcare professional to which the individual healthcare professional field 1020A-1020G corresponds may be contained. In one such embodiment, the notes field 1030 may be designed to auto-populate with information 1035 explaining what working conditions 526A-526G are causing the individual healthcare professional to be at an increased risk of committing a medical error 1035 when the individual is at such an increased risk. In some embodiments, the processor 515 may generate, and the screen display 1000 may contain, indicia indicating the team as a whole's risk of committing a medical error based, at least in part, on the workload experienced by and the threshold limits corresponding to the individuals defining the team.

In some embodiments, the method 400 may further comprise updating the displayable indicia 466 to account for changes in the working conditions experienced by an individual or team of healthcare professionals. In such embodiments, the processor 515 may reiterate one or more of the above-described method steps to update or generate new displayable indicia 462-464 and subsequently display the same. The processor 515 may, in some embodiments, reiterate method steps 450-465 in accordance with a defined time schedule. In an embodiment, the time schedule may be such that the processor 515 reiterates steps 450-465 a plurality of times within an hour. In one such embodiment, the time schedule may be such that the processor 515 reiterates steps 450-465 approximately every two minutes. As updated or new displayable indicia 462-464 is generated by the processor 515 and subsequently transmitted to the user interface 511 of the one or more computing devices 510 for display, the screen displays 900, 1000 may update to display the updated or new displayable indicia 462-464 and/or information concerning the individual's or team of individuals' updated experienced working conditions 526A-526G.

For instance, FIG. 9A shows a screen display 900 displaying information pertaining to the working conditions experienced by an individual at a first point in time (Jan. 21, 2018 at 3:00 PM) and what degree such conditions are subjecting the individual to an increased risk of committing a medical error. FIG. 9B shows a screen display 900 corresponding to the working conditions experienced by the individual at a second point in time (Jan. 21, 2018 at 3:002 PM) two minutes after the first point in time and what degree such conditions are subjecting the individual to an increased risk or committing a medical error. During the two minute interval between the first point in time and the second point in time, the individual experienced increases in both the number of patients cared for and the number of call light counts incurred, as evidenced by the comparison of FIGS. 9A and 9B. To reflect the foregoing changes in the individual's experienced working conditions during the two-minute interval, both the patient count field 920B and call light field 920F of the screen display 900 is updated to provide an updated, visual summary of the individual's experienced workload and what degree such workload places the individual at an increased risk for committing a medical error.

As evidenced by the foregoing example, embodiments of the methods 400 and systems 500 of the present disclosure may monitor the working conditions experienced by an individual healthcare professional or team of healthcare professionals and provide displayable indicia indicating whether such working conditions are subjecting the individual or team of individuals to an increased risk of committing a medical error in substantially real time. Accordingly, the methods 400 and systems 500 of the present disclosure may be utilized by healthcare administrators and managers to better identify situations where a healthcare professionals would benefit from additional assistance, a reduced or modified workload, task reassignment, patient reassignment, or work schedule reassignment at, or substantially near, the time in which situations arise. As such, the various methods 400 and systems 500 of the present disclosure may be utilized for a variety of applications within the healthcare field.

The threshold limits 531A-531G generated by the methods 400 and systems 500 disclosed herein may be utilized to assemble or assign a team or unit of healthcare professionals in a manner that reduces the chance the unit or team will commit a medical error their experienced workload. For instance, a healthcare professional having a threshold limit that suggests they are at a higher risk for making a medical related error when experiencing high call light volumes may be placed in a team or unit in which other healthcare professionals are not at a higher risk for making a medical related error when experiencing high call light volumes. In this way, management may create teams of healthcare professionals that as a group have a lower chance of committing a medical related error.

In some embodiments, the methods 400 and systems 500 disclosed herein may be modified or optimized to automatically assign patients to a healthcare professional within a healthcare professional unit or team. For instance, the system may be optimized to assign a patient with a high number of prescribed medications to a healthcare professional with a high medication count threshold limit suggesting the healthcare professional is able to handle large volume of med count duties without being subject to an increased risk of committing a medical error. In other applications or embodiments, the methods 400 and systems 500 disclosed herein may be optimized to balance workloads over multiple healthcare teams or units. For instance, a new patient assignment to a healthcare professional unit may be determined based, at least in part, on what percentage of the staff defining a prospective team or unit is at an elevated risk levels for committing a medical error based on their current workload. A healthcare professional unit with a lower percentage of staff being at an increased risk of committing a medical related error may be assigned the new patient. In some embodiments, the methods 400 and systems 500 of the present disclosure may be adapted to recommend that a user 505 with sufficient permissions assign a patient to a healthcare professional or healthcare professional unit. For instance, in an embodiment, the system may be adapted to recommend to a charge nurse to assign a patient to a healthcare professional having a high patient count threshold limit during a period of time in which high patient volumes are experienced.

To access or retrieve information stored within the system's 500 one or more data repositories, users 505 may be required to make a request to access or retrieve such data via the user interface 511 of the one or more computing devices 510. To guard the system's 500 one or more data repositories from unwanted manipulation, access to the one or more data repositories may be granted or denied by the processor 515, in some embodiments, based on the processor's 515 verification of a user's 505 permission level in one or more user-verification steps 410, 435. If the user's 505 permission level is sufficient, the processor 515 may permit the user 505 to access to access, modify, and/or retrieve information within the one or more data repositories. Conversely, if the user's 505 permission level is insufficient, the processor 515 is configured to deny the user 505 such access.

Figure 6:
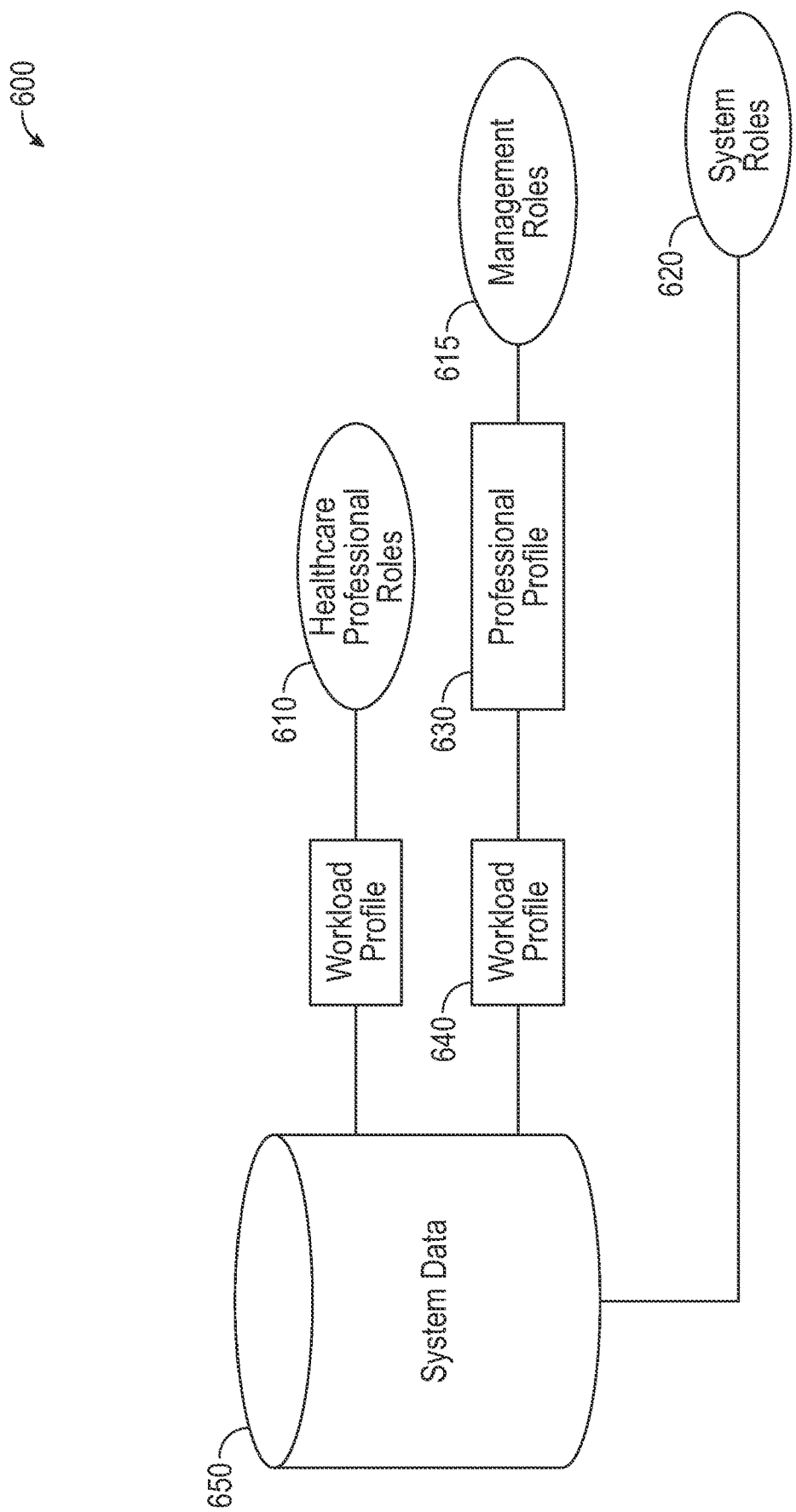
FIG. 6 is a diagram illustrating the manner in which individual access to data in some embodiments of the system may be limited based on user roles.

In a preferred embodiment, user permission levels 600 are based on healthcare professional roles 610, management roles 615, and system roles 620, as shown in FIG. 6. Professional roles 610 may allow users with such roles to access workload profiles 640 within the first database 525. Professional roles 610 may also allow users to access the screen displays 900-1000 on which the displayable indicia generated by the processor 515 may be displayed. In some embodiments, management roles 615 may allow users with such roles to access workload profiles 640 within the first database 525, access professional profiles 630 within the first database 525 or second database 530, permit access to and editing of threshold limits 531A-531G, and allow such users to access the screen displays 900-1000 on which the displayable indicia generated by the processor 515 may be displayed. System roles 620 may allow users with such roles to access system-wide data 650, including professional profiles 630, workload profiles 640, access to and editing of threshold limits 531A-531G, and allow such users to access the screen displays 900-1000 on which the displayable indicia generated by the processor 515 may be displayed. In a preferred embodiment, access to the threshold limits 531A-531G may be limited only to those users 505 having managerial roles 615 or system roles 620 associated therewith. In some instances, management may also serve as an administrator. Prior to finalizing any changes made within the user interface 511 by users 505 having access thereto, the user 505 may be presented with one or more prompts to confirm the user's desire to finalize the selections made in a selection confirmation step.

As described above, in some instances, management may create professional profiles 531 by inputting data into the user interface 511 of the one or more computing devices 510. In some embodiments, to access the professional profiles through the user interface 511, a user 505 may be required to make user request to the processor 515 to access the professional profile 531 within the management control interface 511. In some embodiments, the processor 515 may grant or deny the request based on the permission levels 600 associated with the requesting user 505. In an embodiment, only users 505 having appropriate management roles 615 or system roles 620 may access the threshold limits 531A-531G stored within the system 500. In one embodiment, management roles 615 may be limited to the managers, charge nurses, or other healthcare professionals with managerial control over a hospital floor or wing. A system administrator may also have management roles 615. Individuals assigned system roles 620 are preferably limited to those individuals charged with managing the system 500 and the data contained therein. Upon submitting a user request to access threshold limits 531A-531G stored within the system 500, the processor 515 may verify the user's permission levels 600 by comparing the type of role associated with the user 505 and the type of role required for access to the professional profile 531 and subsequently grant or deny access based on such comparison.

Although the system and method of the present disclosure have been discussed for use within the medical field, one of skill in the art will appreciate that the inventive subject matter disclosed herein may be utilized in other fields or for other applications in monitoring and assessment of an individual's or team of individuals' workload is needed.

The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow depicted in the accompanying figures and/or described herein do not necessarily require the particular order shown, or sequential order, to achieve desirable results. It will be readily understood to those skilled in the art that various other changes in the details, materials, and arrangements of the parts and method stages which have been described and illustrated in order to explain the nature of this inventive subject matter can be made without departing from the principles and scope of the inventive subject matter.

What is claimed is:

1. A system for managing patient load comprising,
a computing device having a user interface,
wherein said user interface is configured to display at least one displayable indicia that indicates a risk level,
wherein said risk level represents a chance an individual has of committing a medical related error while providing healthcare services to a plurality of patients based on workload data,
wherein said workload data includes data representing one or more working conditions experienced by said individual over a period of time,
a processor operably connected to said computing device,
a scanning device operably connected to said processor and configured to read barcodes containing workload data associated with said plurality of patients,
wherein said scanning device transmits said workload data contained within said barcodes to said processor,
a database operably connected to said processor and configured to store said workload data within a workload profile of said individual,
wherein said workload profile is associated with said individual,
a power supply, and
a non-transitory computer-readable medium coupled to said processor and having instructions stored thereon, which, when executed by said processor, cause said processor to perform operations comprising:
receiving said workload data associated with said individual,
retrieving near miss data associated with said individual, said near miss data including data representing one or more instances of an averted medical error over said period of time,
calculating at least one threshold limit for each of said one or more working conditions based on said workload data and said near miss data,
retrieving said workload data from said scanning device,
adding said workload data from said scanning device to current workload data, said current workload data including data representing said one or more working conditions experienced by said individual in real time,
comparing said current workload data to said at least one threshold limit, and
generating said at least one displayable indicia for display in said user interface to indicate said risk level of said individual.

2. The system of claim 1, wherein said risk level is updated as said workload data is received by said processor from said scanning device.

3. The system of claim 1, wherein said risk level is updated after a specified time interval.

4. The system of claim 1, wherein said workload data comprises at least one of task count data, patient count data, acuity score data, work schedule data, medication count data, call light count data, and hours worked data.

5. The system of claim 1, wherein said near miss data comprises at least one of wrong patient data, wrong dose time data, wrong medication data, and incorrect dosage data.

6. The system of claim 1, wherein said database comprises at least one of an Electronic Health Record, Barcoded Medication Administration Record, and Call Light System.

7. The system of claim 1, wherein said workload profile is associated with a professional profile of said individual, wherein said professional profile contains said at least one threshold limit.

8. The system of claim 1, wherein said individual is part of a group of individuals, wherein each said individual within said group of individuals has said workload profile containing said workload data, wherein each said individual within said group of individuals has a professional profile containing said at least one threshold limit.

9. The system of claim 8, wherein said at least one threshold limit of each said individual within said group of individuals is combined to create at least one group threshold limit.

10. The system of claim 9, wherein said current workload data of said group of individuals is compared to said at least one group threshold limit.

11. A non-transitory computer-readable medium coupled to a processor and having instructions stored thereon, which, when executed by said processor, cause said processor to manage patient load of an individual by executing steps comprising:
receiving workload data from a computing device,
wherein a user interface of said computing device is configured to receive workload data related to a plurality of patients,
wherein said workload data includes data representing one or more working conditions experienced by an individual providing healthcare services to said plurality of patients,
saving said workload data to a workload profile having said workload data,
wherein said workload profile is associated with a professional profile of said individual,
wherein said professional profile comprises at least one threshold limit corresponding to said workload data and near miss data,
wherein said at least one threshold limit represents a quantitative threshold corresponding to an amount of said one or more working conditions that said individual can endure before being subject to an increased risk for committing a medical related error,
retrieving said workload data from said workload profile,
retrieving said at least one threshold limit of said professional profile associated with said workload profile,
determining a risk level using said workload data and said at least one threshold limit,
wherein said risk level represents an extent to which said individual is subject to said increased risk for committing said medical related error,
wherein said risk level is updated as said workload data is received by said processor from a scanning device operably connected thereto,
wherein said scanning device is configured to scan barcodes associated with said plurality of patients, wherein said barcodes contain said workload data, and
generating at least one displayable indicia for display in said user interface using said risk level.

12. The non-transitory computer-readable medium of claim 11, further comprising additional instructions, which, when executed by said processor, cause said processor to perform additional operations comprising:
updating said risk level after a specified time interval.

13. The non-transitory computer-readable medium of claim 11, wherein said workload data comprises at least one of task count data, patient count data, acuity score data, work schedule data, medication count data, call light count data, and hours worked data.

14. The non-transitory computer-readable medium of claim 11, wherein said near miss data comprises at least one of wrong patient data, wrong dose time data, wrong medication data, and incorrect dosage data.

15. The non-transitory computer-readable medium of claim 11, further comprising additional instructions, which, when executed by said processor, cause said processor to perform additional operations comprising:
    transmitting said workload data to a database configured to store said workload data within said workload profile of said individual,
        wherein said database comprises at least one of an Electronic Health Record, Barcoded Medication Administration Record, and Call Light System.

16. A non-transitory computer-readable medium coupled to a processor and having instructions stored thereon, which, when executed by said processor, cause said processor to manage patient load of a group of individuals by executing steps comprising:
    receiving workload data from a computing device,
        wherein a user interface of said computing device is configured to receive workload data of an individual within a group of individuals,
        wherein said group of individuals provide healthcare services to said plurality of patients,
    saving said workload data to a workload profile of said individual,
        wherein each workload profile of a plurality of workload profiles is associated with a specific individual within said group of individuals,
        wherein said workload data of said plurality of workload profiles of said group of individuals represents one or more working conditions created by said plurality of patients,
    retrieving said workload data of said plurality of workload profiles of said group of individuals,
        wherein each workload profile of said plurality of workload profiles is associated with a professional profile of a plurality of professional profiles,
        wherein each said professional profile of said plurality of professional profiles comprises at least one threshold limit corresponding to said workload data,
        wherein said at least one threshold limit represents a quantitative threshold corresponding to an amount of said one or more working conditions that said specific individual can endure before being subject to an increased risk for committing a medical related error,
    combining said at least one threshold limit of said plurality of workload profiles to create at least one group threshold limit,
        wherein said at least one group threshold limit represents said quantitative threshold corresponding to said amount of said one or more working conditions that said group of individuals can endure before being subject to said increased risk for committing said medical related error,
    determining a risk level for said group of individuals using said workload data of said group of individuals and said at least one group threshold limit,
        wherein said risk level represents an extent to which said group of individuals is subject to said increased risk for committing said medical related error, and
    generating at least one displayable indicia for display on said user interface based on said risk level,
        wherein said at least one displayable indicia signifies a risk level said group of individuals has of committing said medical related error.

17. The non-transitory computer-readable medium of claim 16, further comprising additional instructions, which, when executed by said processor, cause said processor to perform additional operations comprising:
    updating said risk level after a specified time interval.

18. The non-transitory computer-readable medium of claim 16, wherein said workload data comprises at least one of task count data, patient count data, acuity score data, work schedule data, medication count data, call light count data, and hours worked data.

19. The non-transitory computer-readable medium of claim 16, further comprising additional instructions, which, when executed by said processor, cause said processor to perform additional operations comprising:
    receiving said workload data from a scanning device,
        wherein said scanning device is configured to scan barcodes containing said workload data associated with said plurality of patients, and
    updating said risk level as said workload data is received from a scanning device.

20. The non-transitory computer-readable medium of claim 16, further comprising additional instructions, which, when executed by said processor, cause said processor to perform additional operations comprising:
    transmitting said workload data to a database configured to store said workload data within said workload profile of said individual,
    wherein said database comprises at least one of an Electronic Health Record, Barcoded Medication Administration Record, and Call Light System.

* * * * *